US012797608B2

(12) United States Patent
Kim et al.

(10) Patent No.: US 12,797,608 B2
(45) Date of Patent: Nov. 17, 2026

(54) DIFFUSER AND HAIRDRYER COMPRISING SAME

(71) Applicant: LG ELECTRONICS INC., Seoul (KR)

(72) Inventors: Kyoungtae Kim, Seoul (KR); Hyunchul Kim, Seoul (KR); Yunhee Ku, Seoul (KR); Seungyeon Song, Seoul (KR); Dongwon Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 257 days.

(21) Appl. No.: 18/726,988

(22) PCT Filed: Jan. 17, 2022

(86) PCT No.: PCT/KR2022/000794
§ 371 (c)(1),
(2) Date: Jul. 5, 2024

(87) PCT Pub. No.: WO2023/136381
PCT Pub. Date: Jul. 20, 2023

(65) Prior Publication Data
US 2026/0175024 A1 Jun. 25, 2026

(51) Int. Cl.
*A61N 1/30* (2006.01)
*A45D 20/12* (2006.01)
(Continued)

(52) U.S. Cl.
CPC ........... *A61N 1/303* (2013.01); *A45D 20/122* (2013.01); *A61N 1/0428* (2013.01);
(Continued)

(58) Field of Classification Search
CPC .... A61N 1/303; A61N 1/0428; A61N 1/0436; A61N 1/044; A61N 1/30; A61N 5/0617;
(Continued)

(56) References Cited

U.S. PATENT DOCUMENTS

2005/0251242 A1* 11/2005 Bousfield ............ A61N 5/0617 607/150
2021/0315354 A1* 10/2021 Kim ...................... A45D 20/12

FOREIGN PATENT DOCUMENTS

JP 2021-146151 A 9/2021
KR 10-2002-0093665 A 12/2002
(Continued)

*Primary Examiner* — Eugene T Wu
(74) *Attorney, Agent, or Firm* — Birch, Stewart, Kolasch & Birch, LLP

(57) ABSTRACT

A hairdryer comprises: a body part which includes, at the front thereof, a gas discharge portion through which gas is discharged to the outside; and a diffuser which is detachably coupled to the front of the body part, into which gas discharged from the gas discharge portion is introduced, and which discharges the gas introduced therein to the outside, wherein the diffuser comprises: a circuit board which includes a pogo pin protruding in the forward direction; a discharge cover which is coupled to the front side of a diffusing case and includes a gas discharge hole, a plurality of massage protrusions protruding forward, and a plurality of iontophoresis electrodes comprising a metallic material; and an electrode connector which is positioned between the discharge cover and the circuit board and electrically connects the pogo pin and the iontophoresis electrodes to each other. The hairdryer enables easy attachment/detachment of the discharge cover and thus is easy to manage.

14 Claims, 11 Drawing Sheets

(51) Int. Cl.

| | |
|---|---|
| ***A61N 1/04*** | (2006.01) |
| ***A61N 5/06*** | (2006.01) |
| *A61N 5/067* | (2006.01) |

(52) U.S. Cl.
CPC ........... *A61N 1/0436* (2013.01); *A61N 1/044* (2013.01); *A61N 1/30* (2013.01); *A61N 5/0617* (2013.01); *A45D 2200/202* (2013.01); *A45D 2200/205* (2013.01); *A61N 2005/0627* (2013.01); *A61N 2005/0644* (2013.01); *A61N 2005/0652* (2013.01); *A61N 5/067* (2021.08)

(58) Field of Classification Search
CPC .... A61N 2005/0627; A61N 2005/0644; A61N 2005/0652; A61N 5/067; A61N 1/04; A61N 5/06; A61N 2005/0642; A61N 5/0616; A45D 20/122; A45D 2200/202; A45D 2200/205; A45D 20/10; A45D 20/12; A45D 2200/155; A61B 5/00; A61B 5/0537; A61B 5/446; A61H 39/04; F24H 3/00; F24H 9/2071; G05D 23/19
See application file for complete search history.

(56) References Cited

FOREIGN PATENT DOCUMENTS

| | | | |
|---|---|---|---|
| KR | 10-2020-0033127 | A | 3/2020 |
| KR | 10-2021-0076249 | A | 6/2021 |
| KR | 10-2021-0126343 | A | 10/2021 |

* cited by examiner (a)

(b)

Arndt-Schultz Energy graph

DIFFUSER AND HAIRDRYER COMPRISING SAME

CROSS REFERENCE TO RELATED APPLICATION

This application is the National Phase of PCT International Application No. PCT/KR2022/000794, filed on Jan. 17, 2022, which is hereby expressly incorporated by reference into the present application.

Technical Field

The present disclosure relates to a diffuser and a hair dryer including the same, more particularly, to a diffuser coupled to a main body of a hair dryer to provide gas to a user and the hair dryer including the same.

Background Art

When removing moisture from wet hair of a human body as much as desired or when styling the hair from a current shape to a desired shape, a hair dryer that discharges gas through a gas outlet may be used.

In one example, the hair dryer may provide gas characteristics desired by a user, such as a gas temperature, a gas speed, a gas flow area, and the like through a diffuser. The diffuser may be coupled to a main body of the hair dryer to change the gas characteristics and provide the changed gas characteristics to the user. Further, the diffuser may include care means such as a massage protrusion to manage a scalp health and the like of the user.

In connection, Korean Utility Model Application Publication No. 20-2011-0002484 discloses a diffuser disposed in a hair dryer. The diffuser disclosed in the above document discloses a massage protrusion that may perform user's scalp and hair care.

The diffuser may include various components to manage or care for scalp and hair in addition to the massage protrusion.

In one example, depending on conditions of the user's scalp and hair, uniform application of the means provided for the management of the user's scalp or hair may degrade efficiency or ease of use.

Therefore, it is an important task in the technical field to provide various means for the management and care of the user's scalp or hair, and further to provide appropriate care means based on the conditions of the user's scalp or hair.

DISCLOSURE

Technical Problem

Embodiments of the present disclosure are intended to provide a diffuser and a hair dryer including the same capable of effectively managing scalp and hair of a user.

In addition, embodiments of the present disclosure are intended to provide a diffuser and a hair dryer capable of effectively identifying moisture conditions of user's scalp and hair.

In addition, embodiments of the present disclosure are intended to provide a diffuser and a hair dryer capable of improving ease of use and efficiency by providing appropriate care means based on conditions of user's scalp and hair.

Technical Solutions

In accordance with an aspect of the present disclosure, a hair dryer may include: a main body including a gas outlet disposed at a front side of the main body so that gas is discharged outside through the gas outlet; a handle extending from the main body; and a diffuser detachably coupled to the front side of the main body so that gas discharged from the gas outlet flows into the diffuser and is then discharged outside. The diffuser may include: a diffusing case, a rear side of which is coupled to the main body, configured to enable gas discharged from the gas outlet to flow into the diffusing case; a circuit board including at least one pogo pin that is located at a front surface of the diffusing case and protrudes forward; a discharge cover coupled to the front side of the diffusing case and configured to include at least one gas discharge hole, a plurality of massage protrusions protruding forward, and a plurality of iontophoresis electrodes formed of a metal material; and an electrode connector disposed between the discharge cover and the circuit board and configured to electrically connect the pogo pin to the iontophoresis electrodes.

The electrode connector may include: a connection frame; and a connection electrode configured to include a ring electrode located in a backward direction of the connection frame and a branch electrode extending radially from the ring electrode.

The connection frame may be formed in a ring shape that has an opening at a center thereof.

The hair dryer may further include: a proximity sensor mounted on the circuit board and exposed through the opening of the connection frame.

The connection electrode may include: a first connection electrode coupled to the connection frame; and a second connection electrode coupled to the connection frame so as not to contact the first connection electrode.

The ring electrode of the first connection electrode may be located inside the ring electrode of the second connection electrode; and the branch electrode of the first connection electrode may extend radially after being bent in a forward direction and may be disposed at a position different from that of the branch electrode of the second connection electrode in forward and backward directions.

The pogo pin may include: a first pogo pin connected to the ring electrode of the first connection electrode; and a second pogo pin connected to the ring electrode of the second connection electrode, wherein the first pogo pin and the second pogo pin are connected to power sources having different polarities.

The iontophoresis electrode may include: a first iontophoresis electrode connected to the first connection electrode; and a second iontophoresis electrode connected to the second connection electrode, wherein a length of a protrusion from a back surface of the first iontophoresis electrode is shorter than a length of a protrusion from a back surface of the second iontophoresis electrode.

The branch electrode may be made of a metal material having elasticity.

The iontophoresis electrode may include: a first iontophoresis electrode connected to a power source having a positive(+) polarity; a second iontophoresis electrode connected to a power source having a negative(−) polarity; and a controller configured to measure the amount of moisture in a scalp by measuring impedance between the first iontophoresis electrode and the second iontophoresis electrode.

The hair dryer may further include: a temperature adjuster configured to control a temperature of the gas discharged through the gas outlet, wherein the controller controls the temperature adjuster so that the temperature of the gas discharged through the gas outlet increases as the amount of moisture increases.

The hair dryer may further include: a fan unit configured to control a speed of the gas discharged through the gas outlet, wherein the controller controls the fan unit so that the speed of the gas discharged through the gas outlet increases as the amount of moisture increases.

The controller may reduce the amount of current flowing through the iontophoresis electrode as the amount of moisture increases.

The hair dryer may further include: a light irradiator provided inside the diffusing case, and configured to emit light in a direction of the discharge cover, wherein the controller controls the light irradiator so that the amount of light emitted by the light irradiator increases as the amount of moisture increases.

The hair dryer may further include: a light irradiator provided inside the diffusing case, and configured to emit light in a direction of the discharge cover; and a controller configured to deactivate the light irradiator when cumulative care energy generated depending on the amount of light emitted from the light irradiator and a used time of the light irradiator exceeds a reference value.

Advantageous Effects

Embodiments of the present disclosure may provide the diffuser and the hair dryer including the same capable of effectively managing the scalp and the hair of the user.

In addition, the hair dryer according to the embodiments of the present disclosure can allow a discharge cover to be easily detachably coupled thereto, so that the hair dryer provided with the discharge cover can be easily managed.

In addition, embodiments of the present disclosure may provide the diffuser and the hair dryer capable of effectively identifying the conditions of the user's scalp and hair.

In addition, embodiments of the present disclosure may provide the diffuser and the hair dryer capable of improving the ease of use and the efficiency by providing the appropriate care means based on the conditions of the user's scalp and hair.

BEST MODE

Figure 1:
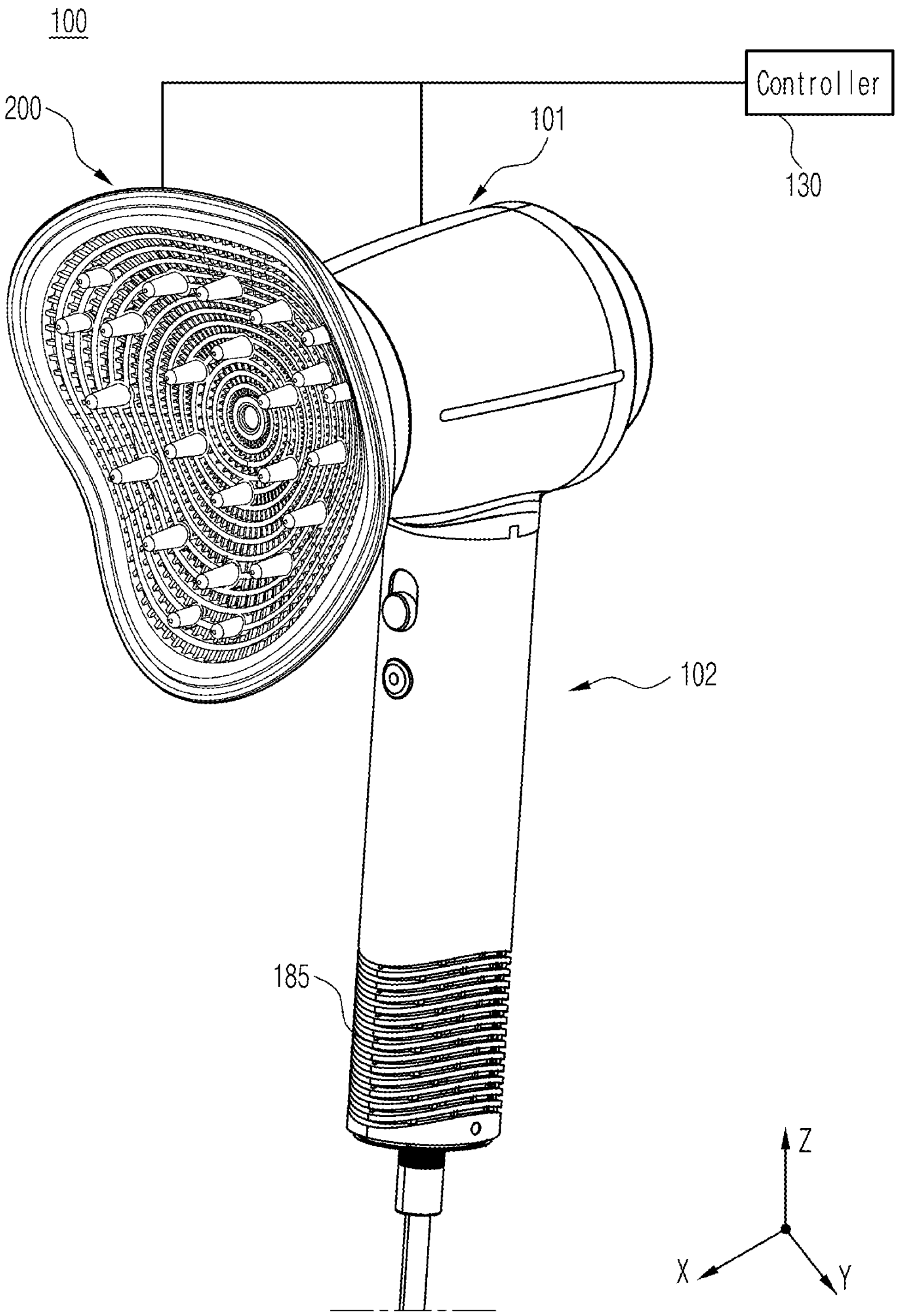
FIG. 1 is a view showing a hair dryer according to an embodiment of the present disclosure.

Hereinafter, an embodiment of the present disclosure will be described in detail with reference to the accompanying drawings to be easily implemented by those skilled in the art to which the present disclosure belongs.

However, the present disclosure may be implemented in many different forms and is not limited to embodiments described herein. In addition, in order to clearly describe the present disclosure, components irrelevant to the description are omitted, and like reference numerals are assigned to similar components throughout the specification.

In this specification, duplicate descriptions of the same components are omitted.

Further, in this specification, it will be understood that when a component is referred to as being "connected with" another component, the component may be directly connected with the other component or intervening components may also be present. In contrast, it will be understood that when a component is referred to as being "directly connected with" another component in this specification, there are no intervening components present.

Further, in this specification, the terminology used herein is for the purpose of describing a specific embodiment only and is not intended to be limiting of the present disclosure.

Further, in this specification, the singular forms "a" and "an" are intended to include the plural forms as well, unless the context clearly indicates otherwise.

Further, in this specification, it will be further understood that the terms "comprises", "comprising", "includes", and "including" specify the presence of the certain features, numbers, steps, operations, elements, and parts or combinations thereof, but do not preclude the presence or addition of one or more other features, numbers, steps, operations, elements, and parts or combinations thereof.

Further, in this specification, the term 'and/or' includes a combination of a plurality of listed items or one of the plurality of listed items. In this specification, 'A or B' may include 'A', 'B', or 'both A and B'.

Figure 2:
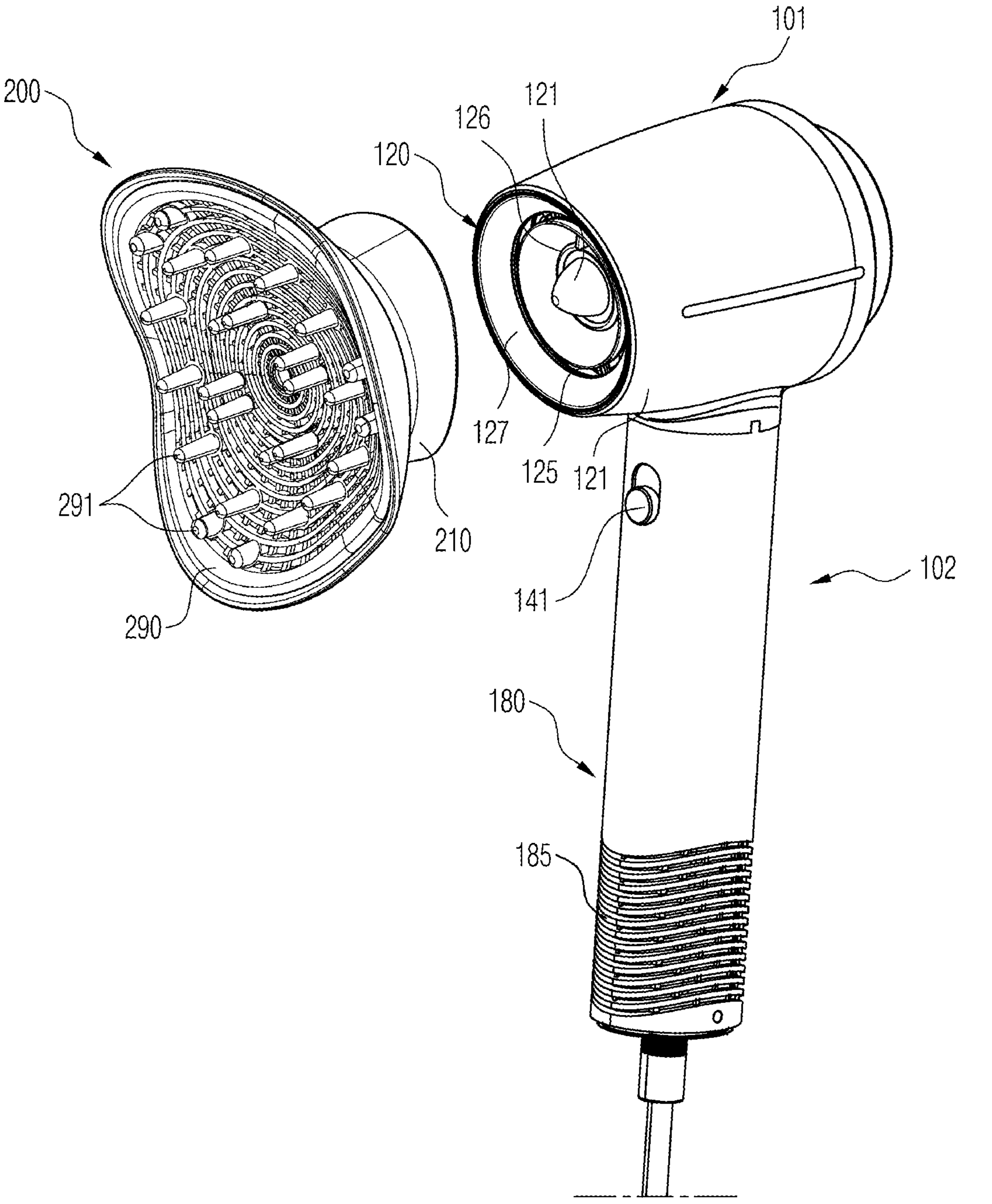
FIG. 2 is a view showing a state in which a diffuser is separated from a hair dryer according to an embodiment of the present disclosure.

FIG. 1 is a view showing a hair dryer 100 according to an embodiment of the present disclosure. FIG. 2 is a view showing a state in which a diffuser 200 is separated from the hair dryer 100 shown in FIG. 1. Further, FIG. 3 is a view showing an internal cross-section of the hair dryer 100 shown in FIG. 2.

The hair dryer 100 according to an embodiment of the present disclosure includes a main body 101, a handle 102, and a diffuser 200 as shown in FIG. 1. In addition, as shown in FIG. 2, the main body 101 includes a gas outlet 120 through which gas introduced from outside is discharged.

Figure 3:
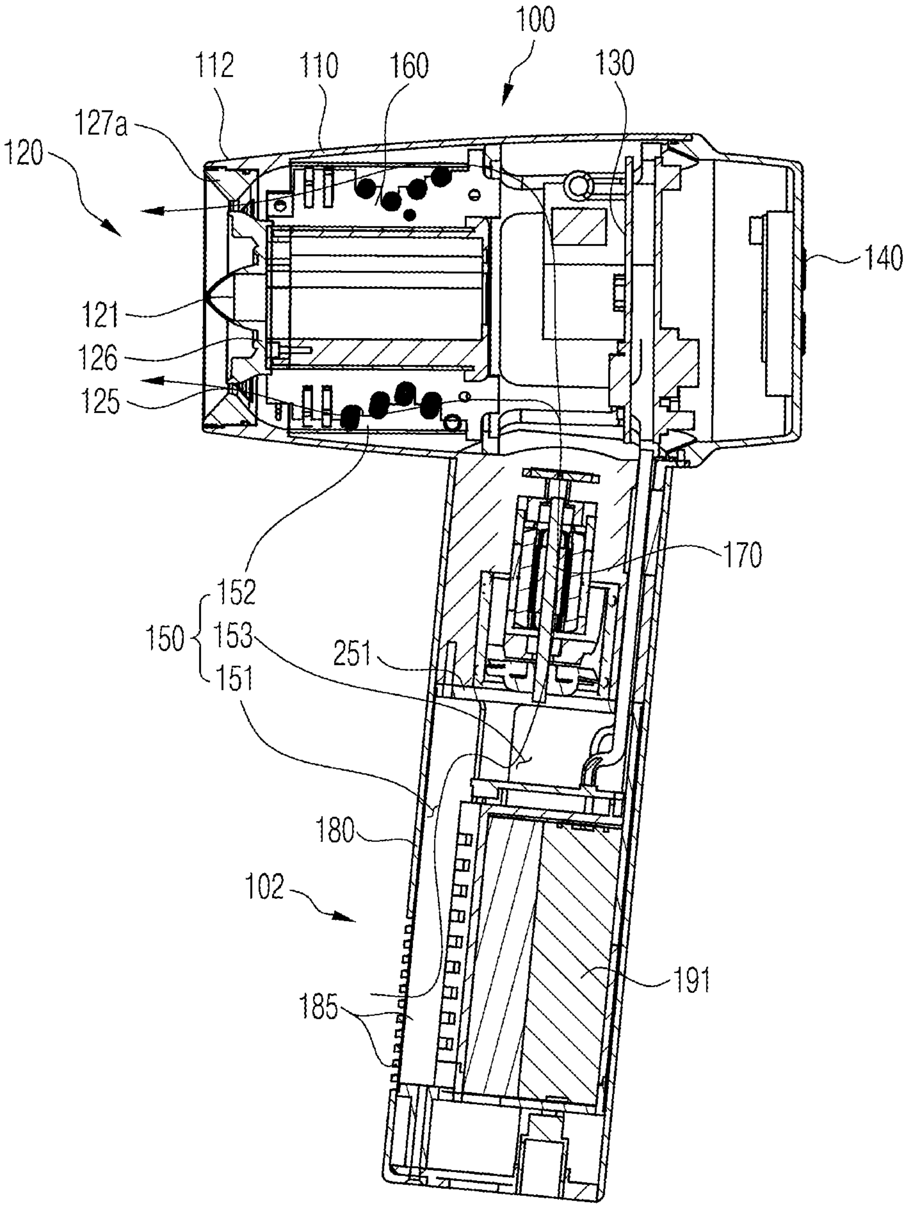
FIG. 3 is a view showing an internal cross-section of a hair dryer shown in FIG. 2.

As shown in FIG. 3, the main body 101 may include a gas flow path 150 through which the gas flows may be defined therein and the gas outlet 120 through which internal gas is discharged to the outside. The main body 101 may have an extended shape along a front and rear direction and may have various cross-section shapes such as circular or polygonal shapes when viewed from the front.

In the present disclosure, front, rear, left, right, top, and bottom definitions may be made centering on the main body 101. For example, referring to FIG. 2, the gas outlet 120 may be disposed at a front side of the main body 101, and the handle 102 may have a shape extending substantially downward from the main body 101.

The gas flowing inside the main body 101 may be introduced through a gas inlet, and the gas inlet 185 may be disposed on the main body 101 or the handle 102. As shown in FIGS. 1 to 3, when the gas inlet 185 is disposed on the handle 102, the gas flow path 150 may extend from the handle 102 to the main body 101, specifically, from the gas inlet 185 to the gas outlet 120.

The gas may be introduced from the outside through the gas inlet 185 disposed on the main body 101 or the handle 102, and the introduced gas may flow along the gas flow path 150 and be discharged to the outside through the gas outlet 120.

The handle 102 may extend from the main body 101. Referring to FIGS. 1 to 3, the handle 102 extending substantially downward from the main body 101 is illustrated. The handle 102 may be integrally molded with the main body 101, or separately manufactured from the main body 101 and coupled to the main body 101.

When the handle 102 is manufactured separately from the main body 101 and coupled to the main body 101, the handle 102 may be disposed such that a longitudinal direction thereof with respect to the main body 101 is fixed or variable.

For example, the handle 102 may have a hinge coupling portion, and may be coupled to the main body 101 such that the longitudinal direction of the handle 102 is changeable, that is, the handle 102 is foldable relative to the main body 101.

The handle 102 may be a portion grabbed by a hand of a user, and thus may have a shape for improving grip convenience. The extending direction of the handle 102 may vary. However, for convenience of description below, the direction in which the handle 102 extends from the main body 101 will be described as a downward direction.

Referring to FIG. 3, the hair dryer 100 according to an embodiment of the present disclosure includes a fan 170 capable of flowing the gas and adjusting a speed of the discharge gas discharged through the gas outlet 120. The fan 170 may be disposed on the gas flow path 150 to flow the gas and may be disposed inside the main body 101 or inside the handle 102.

For example, when the gas inlet 185 is disposed on the handle 102, the gas flow path 150 may extend from the gas inlet 185 of the handle 102 to the gas outlet 120 of the main body 101, and the fan 170 may be disposed on the gas flow path 150 located in the handle 102.

In addition, a temperature adjuster 160 that may adjust a temperature of the discharge gas may be disposed inside the main body 101. The temperature adjuster 160 may be disposed in various forms and may be disposed at various positions. In FIG. 2, the temperature adjuster 160 disposed inside the main body 101 is schematically illustrated.

In addition, the temperature adjuster 160 may be disposed in various types. The temperature adjuster 160 may be in a scheme of heating the gas by providing current to a coil-shaped resistor to generate heat.

However, the resistor of the temperature adjuster 160 may not necessarily be in the shape of the coil, and may be disposed in various types, such as a thermoelement, capable of heating the gas or adjusting the temperature of the gas.

A method for operating the hair dryer 100 according to an embodiment of the present disclosure will be schematically described with gas flow.

First, the user manipulates a power button 141 disposed on the main body 101 or the handle 102. When the power button 141 is turned on, the gas is introduced into the hair dryer 100 through the gas inlet 185 as the fan 170 is operated.

The gas introduced through the gas inlet 185 flows along the gas flow path 150 by the fan 170 toward the gas outlet 120, and the discharge gas is discharged from the gas outlet 120 to be provided to the user. In this process, a flowing speed of the gas on the gas flow path 150 may be adjusted by the fan 170 and a temperature of the gas on the gas flow path 150 may be adjusted by the temperature adjuster 160.

As shown in FIG. 1, the hair dryer 100 may receive power by connecting a power cable to a lower end of the handle 102.

Alternatively, the hair dryer 100 may include a battery module 191 so that the hair dryer 100 can be used wirelessly. When the battery module 191 is placed in the main body 100, the weight of the hair dryer 100 increases and the usability of the hair dryer 100 decreases, so that the battery module 191 can be placed in the handle 102 as shown in FIG. 3.

Since the weight of the battery module 191 is greater than the fan unit 170 disposed in the handle 102, the battery module 191 is located under the handle 102 and the fan unit 170 is located on the handle 102.

In particular, when using the battery module 191, the voltage from the battery module 191 is lower than the voltage generated when the hair dryer 100 is driven by connecting to a power source. When using the hair dryer 100 wirelessly, DC power of about 10V is used, when using the hair dryer 100 wired, AC voltage of about 215V is used.

When driving the fan unit 170 with the low-voltage power of the battery module 191, the fan unit 170 can be driven by increasing the voltage using a boosting module that can increase the voltage to obtain sufficient airflow strength.

Since the battery module 191 generates heat, heat can be cooled by placing the battery module 191 on the gas flow passage 150 through which fluid passes. Since the battery module 191 is located in the handle 102, the battery module 191 can be located on the first flow path located in the handle 102.

Figure 4:
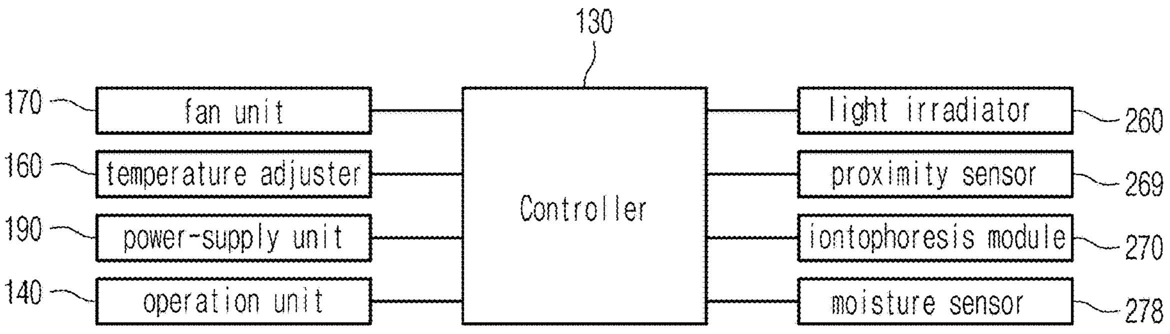
FIG. 4 is a block diagram illustrating a configuration connected to the controller of a hair dryer according to an embodiment of the present disclosure.

Meanwhile, referring to FIG. 4, the hair dryer 100 according to an embodiment of the present disclosure may include a controller 130. The controller 130 may be connected not only to a fan unit 170, a temperature adjuster 160, a power-supply unit 190, and an operation (or manipulation) unit 140, but also to a light irradiator 260, a proximity sensor 269, and an iontophoresis module 270 of the diffuser 200 which will be described later, such that the controller 130 can control the above-described components.

The controller 130 may be disposed on one of the diffuser 200, the main body 101, and the handle 102. Alternatively, the controllers 130 may be respectively arranged on all of the diffuser 200, the main body 101, and the handle 102. For example, as shown in FIG. 3, the controller 130 may be disposed on the main body 101 to be signally connected to the diffuser 200, or the plurality of controllers 130 may be respectively arranged on the diffuser 200 and the main body 101.

Adjusting operating states of the fan 170 and the temperature adjuster 160 may be performed by manipulator manipulation by the user or may be automatically performed based on an operation mode preset in the controller 130.

In addition, when a distance to a target located in front of the diffuser 200 is identified to be equal to or less than a reference distance through the proximity sensor 269 of the diffuser 200, the controller 130 may control the light irradiator 260 of the diffuser 200 to irradiate light.

The iontophoresis module 270 may insert a material into the scalp using a pair of electrodes. When a pair of iontophoresis electrodes 292 connected to different poles touch the scalp, current flows into the scalp so that moisture can permeate into the scalp along the current, thereby making the skin hard and tight, causing blood to move away from the skin and closing pores of the skin.

Iontophoresis may promote regeneration of the skin by temporarily destroying the calcium ion concentration in the scalp. In order to maximize the effect of the iontophoresis module, such iontophoresis can be used after applying essence such as vitamins to the scalp.

It is desirable to differently control the intensity or temperature of the airflow using the fan unit 170, the intensity of light emitted from the light irradiator, and the voltage of iontophoresis depending on the dry state of the scalp. Therefore, a moisture sensor 278 may be provided to measure the amount of moisture in the scalp.

The moisture sensor can measure dryness of the scalp by using a pair of electrodes to measure the impedance of the material between the pair of electrodes. The more moisture there is on the scalp, the more ionic substances can conduct electrons between electrodes, and the greater the intensity of the electric field.

The greater the intensity of the electric field between two electrodes, the greater the moisture content of the scalp. In addition, as the moisture content of the scalp decreases, the intensity of the electric field may also decrease. Since the impedance appears to be a lower value as the intensity of the electric field increases, it can be determined that the lower the measured impedance value, the greater the moisture content.

The electrodes of the moisture sensor 278 can be additionally provided in the diffuser 200 to measure the moisture content of the scalp and hair. However, in the present embodiment, the moisture content of the scalp can be measured using the iontophoresis electrodes 292 described above.

The iontophoresis electrodes 292 are also implemented as one pair of iontophoresis electrodes 292. Thus, when the electric field is formed by the pair of iontophoresis electrodes 292, as the moisture content of the scalp increases, measured impedance (i.e., bioelectrical resistance) may have a low value, and as the moisture content decreases, measured impedance (i.e., bioelectrical resistance) may have a high value.

In addition, the controller 130 may identify an impedance of the target located in front of the diffuser 200 through the iontophoresis electrode 292 of the diffuser 200, and determine a moisture amount of the target through the impedance. As the moisture amount increases, the controller 130 may control the fan 170 such that the gas speed at the gas outlet 120 increases, control the temperature adjuster 160 such that the gas temperature increases, or control the light irradiator 260 such that a light amount of the light irradiator 260 increases.

In one example, FIG. 2 shows the gas outlet 120 disposed on the main body 101. As shown in FIG. 1 or 3, the main body 101 may have a cross-section in an approximately circular shape and may have a length. However, the cross-section shape of the main body 101 may be varied as needed.

The gas outlet 120 of the hair dryer 100 according to an embodiment of the present disclosure will be described in detail with reference to FIG. 3.

At least a portion of the gas flow path 150 may be defined inside the main body 101, and one side of the main body 101 is opened. For example, the main body 101 may extend in the front and rear direction and a front surface thereof may be opened.

Opened one side of the main body 101 may be in communication with the gas flow path 150. In one example, the gas outlet 120 may be disposed on the main body 101 to shield the opened one side of the main body 101.

The opened one side of the main body 101 may correspond to an end of the gas flow path 150, and the end of the gas flow path 150 may correspond to the gas outlet 120. For example, the gas outlet 120 may be composed of the gas flow path 150 exposed through the open front surface of the main body 101 and an outer wall front end 112 of the main body 101.

In one example, as shown in FIG. 2, in an embodiment of the present disclosure, the gas outlet 120 may include a center portion 126 and side portion 125 through which the gas is discharged. The gas flowing along the gas flow path 150 may be simultaneously delivered to the center portion 126 and the side portion 125 to be discharged to the outside.

The center portion 126 and the side portion 125 may correspond to discharge holes through which the gas is discharged from the gas outlet 120. The center portion 126 may be defined at a central side on the cross-section of the gas outlet 120, and a cross-section shape thereof may be circular. However, a shape of the center portion 126 may be a polygonal shape such as a square and the like as needed, and a size of a diameter thereof may also be varied as needed.

The side portion 125 may be defined to surround the center portion 126. For example, as shown in FIG. 2, the center portion 126 may be defined in a substantially circular shape at the center of the gas outlet 120, and the side portion 125 may be an opening in a shape of a ring in which the center portion 126 is defined at a center thereof.

In the present disclosure, the ring shape may have an extended shape of a closed curve shape. For example, FIG. 2 discloses the side portion 125 having a circular ring shape. The ring shape may not necessarily be circular, and may be, for example, a polygonal ring shape such as a triangle, a square, or the like. That is, in an embodiment of the present disclosure, the side portion 125 may be in the circular ring or the polygonal ring shape, and FIG. 2 shows the side portion 125 having a substantially circular ring shape.

Further, the center portion 126 and the side portion 125 may be in communication with the same gas flow path 150 together. Referring to FIG. 3, there is one gas flow path 150 extending from the handle 102 inside the main body 101. The center portion 126 and the side portion 125 of the gas outlet 120 are in communication with the gas flow path 150 together to discharge the gas at the same time.

The discharge gas discharged from the side portion 125 may form a sense of volume for an entirety of the discharge gas discharged through the gas outlet 120. That is, a cross-sectional area of the entirety of the discharge gas may correspond to a size of a closed cross-section formed by the side portion 125.

However, the discharge gas of the side portion 125 may be diffused while being flowed, and a portion of the gas flow may be distributed toward a center on the cross-section where the gas is not discharged by the side portion 125, and thus, the cross-sectional area of the discharge gas may be reduced.

Accordingly, in an embodiment of the present disclosure, the center portion 126 is defined at a center of the side portion 125, and the phenomenon in which the discharge gas of the side portion 125 is distributed toward the center on the cross-section is suppressed by discharge gas of the center portion 126.

That is, the discharge gas of the center portion 126 flows from the center on the cross-section of the entire discharge gas of the gas outlet 120, and suppresses the discharge gas of the side portion 125 from being distributed toward the center during the flow process, so that it may be advantageous for the entire discharge gas to maintain an initial cross-sectional area thereof.

Accordingly, discharge gas having a large cross-sectional area may be provided to the user, and the user may perform dry using the bulky gas. For example, the entire discharge gas with the volume formed through the center portion 126 and the side portion 125 may allow the user to perform the dry in a larger area.

Further, in an embodiment of the present disclosure, because the center portion 126 and the side portion 125 are in communication with one gas flow path 150, the gas flow paths 150 respectively for the center portion 126 and the side portion 125 may not separately defined. Thus, it may be advantageous in terms of design and may be efficient in providing three-dimensional discharge gas to the user.

In one example, referring to FIG. 2, in an embodiment of the present disclosure, the gas outlet 120 further includes a discharge base 121 disposed on the opened one side of the main body 101. The center portion 126 may be defined at a center of the discharge base 121, and the side portion 125 may be defined between an outer circumferential surface of the discharge base 121 and an outer wall of the main body 101.

FIG. 2 illustrates the discharge base 121 coupled to the opened one side of the main body 101. The discharge base 121 may be disposed to correspond to an opened cross-sectional shape of the one side of the main body 101, but may not be limited thereto and may be formed in various shapes or materials.

For example, the discharge base 121 may be disposed to be partially different from the shape of the opened front surface of the main body 101 to determine the shape of the side portion 125, and may be molded with a material the same as or different from a material of the outer wall of the main body 101.

The discharge base 121 may constitute an entirety or a portion of one surface of the main body 101, for example, the front surface of the main body 101 as shown in FIG. 2, so that the center portion 126 may be defined at the center of the discharge base 121 and the side portion 125 may be defined between the outer circumferential surface of the discharge base 121 and the outer wall of the main body 101.

The discharge base 121 may be coupled to an opening of the main body 101 in various schemes, such as a scheme using a plurality of coupling ribs, and may be integrally molded with the main body 101.

In one example, as shown in FIG. 2, in an embodiment of the present disclosure, the discharge base 121 may have a shape of being indented toward an interior of the main body 101 from the side portion 125 toward the center portion 126.

A center of a front surface of the discharge base 121 may be indented toward the interior of the main body 101, so that the front surface of the discharge base 121 may form a curved surface. Accordingly, the discharge gas of the center portion 126 on the flow path of the discharge gas discharged to the gas outlet 120 may be discharged upstream from the discharge gas of the side portion 125.

When the discharge gas of the center portion 126 on the flow path of the entire discharge gas starts to be diffused prior to the discharge gas of the side portion 125, the cross-section of the discharge gas of the central portion 126 may be increased through the diffusion, and an effect in which the discharge gas of the center portion 126 with an increased cross-sectional area suppresses the discharge gas of the side portion 125 from being flowed or discharged toward the center may be increased.

Further, the front surface of the discharge base 121 constituting a portion of a space in which the discharge gas of the center portion 126 is diffused forms the curved surface, so that it may be advantageous in preventing formation of unnecessary turbulence. A curvature of the curved surface formed by the front surface of the base portion may be variously set as necessary.

In one example, an embodiment of the present disclosure may further include a guide cone disposed at a center of the center portion 126 and guiding the flow of the gas discharged through the center portion 126. The gas may be discharged between an inner surface of the center portion 126 and the guide cone.

FIG. 2 illustrates the guide cone disposed at the center of the center portion 126. As the guide cone is disposed, the discharge gas of the center portion 126 is discharged into a space between the inner surface of the center portion 126 and an outer surface of the guide cone.

When the guide cone is disposed at the center of the center portion 126, the center portion 126 may correspond to a ring-shaped discharge hole. That is, the discharge gas of the center portion 126 may have a ring-shaped cross-section and may be discharged from the center portion 126.

As described above, the discharge gas of the center portion 126 may contribute to suppressing the reduction of the cross-sectional area resulted from the discharge gas of the side portion 125 that flows toward the center in the flow process. In addition, an embodiment of the present disclosure may increase a level at which the discharge gas of the center portion 126 diffuses outward from the cross-section by disposing the guide cone at the center of the center portion 126.

When the cross-sectional area of the discharge gas of the center portion 126 is increased as the guide cone is disposed, the effect of suppressing the phenomenon in which the discharge gas of the side portion 125 flows inward of the cross-section may be increased.

In one example, in the guide cone, a rear end protruding toward the gas flow path 150 and a front end protruding in a discharge direction of the gas of the center portion 126 may respectively have conical shapes. The conical shape means a shape in which a cross-section has a circular shape and a diameter of the circle gradually decreases as a length increases.

However, in the conical shape, the circular shape may include a shape other than a definite circular shape such as an ellipse and the like, and the reduction in the diameter may not necessarily be constant, for example, a diameter reduction rate may gradually increase or gradually decrease.

Further, as the front end of the guide cone protrudes in the conical shape, an effect in which the discharge gas of the center portion 126 is concentrated toward the rim of the center portion 126 increases. Thus, the effect of suppressing the discharge gas of the side portion 125 from flowing toward the discharge gas of the center portion 126 may be further increased.

An outer circumferential surface of the guide cone may have a shape corresponding to an inner circumferential surface of the center portion 126, and a separation distance between the outer circumferential surface of the guide cone and the inner circumferential surface of the center portion 126 may be varied as needed.

Further, the guide cone may be made of a material the same as or different from the material of the discharge base 121, and a curvature of the outer surface thereof may be variously designed as needed.

In one example, the gas outlet 120 may further include a discharge guide ring. The discharge guide ring may be disposed on the inner surface of the center portion 126 and protrude in the discharge direction of the gas of the center portion 126 to guide the gas flow together with the guide cone. FIG. 2 illustrates that the guide cone and the discharge guide ring are arranged in the center portion 126.

The discharge guide ring may have a ring shape extending along the rim of the center portion 126, and may be integrally molded with the discharge base 121 or molded separately from the discharge base 121 to be coupled to the inner circumferential surface of the center portion 126.

The discharge guide ring may protrude outward from the center portion 126 or the discharge base 121 based on the gas discharge direction. The flow of the discharge gas of the center portion 126 may be concentrated between the guide cone and the discharge guide ring by the guide cone and the discharge guide ring protruding from the center portion 126.

A protruding end of the discharge guide ring may have a curved shape to facilitate the gas flow. A diameter of the discharge guide ring may be different for each portion, and the shape thereof may also be varied as needed.

Figure 5:
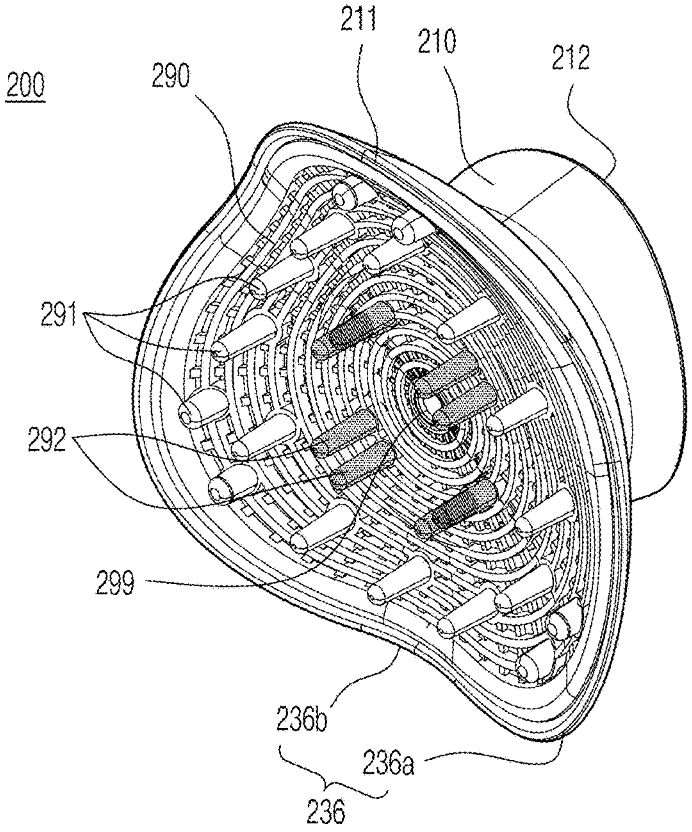
FIG. 5 is a view showing a diffuser according to an embodiment of the present disclosure.

In one example, FIG. 5 shows the diffuser 200 according to an embodiment of the present disclosure. The diffuser 200 is removably coupled to the main body 101, so that the gas discharged from the gas outlet 120 is introduced into the diffuser 200 and the gas introduced into the diffuser 200 is discharged to the outside.

The hair dryer 100 according to an embodiment of the present disclosure may include the diffuser 200 as shown in FIG. 1, and the diffuser 200 may be removably coupled to the main body 101 of the hair dryer 100.

The diffuser 200 may be disposed such that gas discharged from the gas outlet 120 of the main body 101 flows into the diffuser 200. The diffuser 200 may be coupled to the main body 101 such that a rear side thereof covers the gas outlet 120, and the gas discharged from the gas outlet 120 may flow into the diffuser 200 through a gas inlet hole 185 defined at a rear side of the diffuser 200.

The user may selectively use the diffuser 200 for scalp or hair management. For example, the user may use the diffuser 200 including a massage protrusion 291 and a light irradiator 260, which will be described later, for scalp care, or may use the diffuser 200 at which a flow cross-sectional area of the gas is increased as needed in a hair drying step, The rear side of the diffuser 200 may be coupled to the front end 112 of the main body 101. A first coupling portion 127 may be disposed at the front end 112 of the main body 101, and a second coupling portion 220 coupled to the first coupling portion 127 may be disposed at the rear side of the diffuser 200.

A coupling scheme between the diffuser 200 and the main body 101 may vary. The diffuser 200 may be coupled to the main body 101 in a scheme such as screw coupling, fitting coupling, magnetic coupling, sliding coupling, and the like to receive the gas from the main body 101.

An embodiment of the present disclosure may improve ease of use of the user as the diffuser 200 is disposed to be removable from the main body 101. For example, the user may use the hair dryer 100 by removing the diffuser 200 when the user is desired to use the gas discharged from the gas outlet 120 of the main body 101 as it is. Further, the user may use the hair dryer 100 coupled to the diffuser 200 when the user wants a more diffused flow cross-sectional area.

The diffuser 200 may include a diffusing case 210 and a discharge cover 290, and the diffusing case 210 and a discharge cover 290 may form an exterior of the diffuser 200.

An inner diameter of the diffuser 200 may increase the inner diameter in a forward direction. That is, the diffusing case 210 of the diffuser 200 may be disposed such that an internal cross-sectional area thereof viewed from the front increases from a rear side 212 to a front side 211.

Accordingly, the gas delivered from the gas outlet 120 may be provided to the user in a state in which the flow cross-sectional area thereof is increased as the gas speed is reduced in the forward direction of the diffuser 200. The user may use the diffuser 200 for natural drying, styling, and the like of the hair.

The front side 211 of the diffusing case 210 may be opened to define an open front surface. An entirety or a portion of the front surface of the diffuser 200, that is, the diffusing case 210, may define the open surface.

The gas present inside the diffuser 200 may be discharged to the outside through the open surface of the diffusing case 210. That is, the gas inside the diffuser 200 may be provided to the user while being discharged forward through the front side 211 of the diffusing case 210.

In the diffuser 200, the open surface defined in the front side 211 of the diffusing case 210 may be exposed to the outside as it is, or the discharge cover 290 may be provided coupled to the open surface.

FIG. 5 shows a state in which the open surface is present in the front side 211 of the diffusing case 210 according to an embodiment of the present disclosure and the discharge cover 290 is coupled to the open surface.

The discharge cover 290 may be configured to be detachable from the diffusing case 210. Since the discharge cover 290 is removed, hair, etc. introduced into the diffusing case 210 can also be removed.

The discharge cover 290 may be fastened to the diffusing case 210 using screws, etc., or may be fastened to the diffusing case 210 using a coupling structure such as a hook. In addition, the electrode connector 271 connected to the iontophoresis electrodes 292 of the discharge cover 290 can be configured in a detachable form while having a fastening force required to maintain the connection state.

The discharge cover 290 coupled to the open surface defined in the front side 211 of the diffusing case 210 may include a gas discharge hole 298 defined therein through which the gas may be discharged. The discharge cover 290 has a shape corresponding to the open surface of the diffusing case 210 and may be coupled to the diffusing case 210 to be located on the open surface.

A plurality of gas discharge holes 298 may be defined and may be spaced apart from each other in the front surface of the discharge cover 290. FIG. 5 shows the discharge cover 290 in which the plurality of gas discharge holes 298 are uniformly distributed and arranged in the front surface.

Accordingly, in the diffuser, the gas may be discharged through the entirety of the front surface of the discharge cover 290 and the user may receive the gas that is discharged forward of the discharge cover 290 and uniformly dispersed.

The discharge cover 290 may be disposed such that an edge 297 located on the outermost side along a radial direction of the diffuser 200 is in close contact with the diffusing case 238. That is, the diffusing case 210 may have a front circumferential portion 216 surrounding the open surface in the front side 211, and the discharge cover 290 may be disposed such that the edge 297 has a shape corresponding to the front circumferential portion 216 and in contact with the front circumferential portion 216.

As shown in FIG. 5, the diffuser 200 according to an embodiment of the present disclosure may have a first portion 216*a* and a second portion 216*b* on the front circumferential portion 216 of the diffusing case 210. The first portion 216*a* and the second portion 216*b* may be arranged with different distances from the rear side 212 of the diffusing case 210, for example, the gas inlet hole 185 of the diffusing case 210.

In addition, the discharge cover 290 may be disposed such that the edge 297 is molded to correspond to curved shapes of the first portion 216*a* and the second portion 216*b* to be in close contact with the front circumferential portion 216 of the diffusing case 210.

In an embodiment of the present disclosure, the front circumferential portion 216 of the diffusing case 210 and the edge 297 of the discharge cover 290 may be designed to fit a head of the user with an arbitrary curved surface while respectively having curvatures and having different lengths protruding forward along an outer circumferential direction of the diffuser 200. Accordingly, a rate of adhesion with the scalp or the hair of the user may be efficiently increased to minimize a space between the head of the user and the diffuser 200.

Accordingly, an amount of the gas discharged forward of the discharge cover 290 or the light provided by the light irradiator 260 may be efficiently increased.

An ergonomic design is made through the front circumferential portion 216 of the diffusing case 210 and the edge 297 of the discharge cover 290 respectively arranged to form curves when viewed from the side as described above. In this case, the curvatures and the like of the front circumferential portion 216 and the edge 297 may be designed based on a standard head that is statistically determined.

For example, an embodiment of the present disclosure may define a R127 curvature design from a shape of the standard head, and design the shapes of the front circumferential portion 216 and the edge 297 to correspond thereto.

In one example, in an embodiment of the present disclosure, a proximity sensor 269 may be disposed inside the diffusing case 210 to improve ease of use and efficiency of the diffuser 200, and an open region 303 may be defined in the discharge cover 290 such that a distance measurement accuracy of the proximity sensor 269 for the target in front of the diffuser 200, for example, the hair or the scalp of the user may be improved.

That is, the proximity sensor 269 may be in various schemes such as pressure, ultrasound, infrared.

In one example, FIG. 5 shows the discharge cover 290 on which a plurality of massage protrusions 291 are arranged. The massage protrusion 291 may have a pillar shape protruding forward of the diffuser 200 and may press the scalp of the user to provide a massage effect.

A cross-section shape, a protruding length, an arrangement form, and the like of the massage protrusion 291 may be variously determined in terms of a design. An embodiment of the present disclosure provides the user with scalp massage through the massage protrusion 291 while providing the gas diffused through a front surface of the discharge cover 290 to the user, thereby providing the improved ease of use and the scalp and hair care effects.

Figure 6:
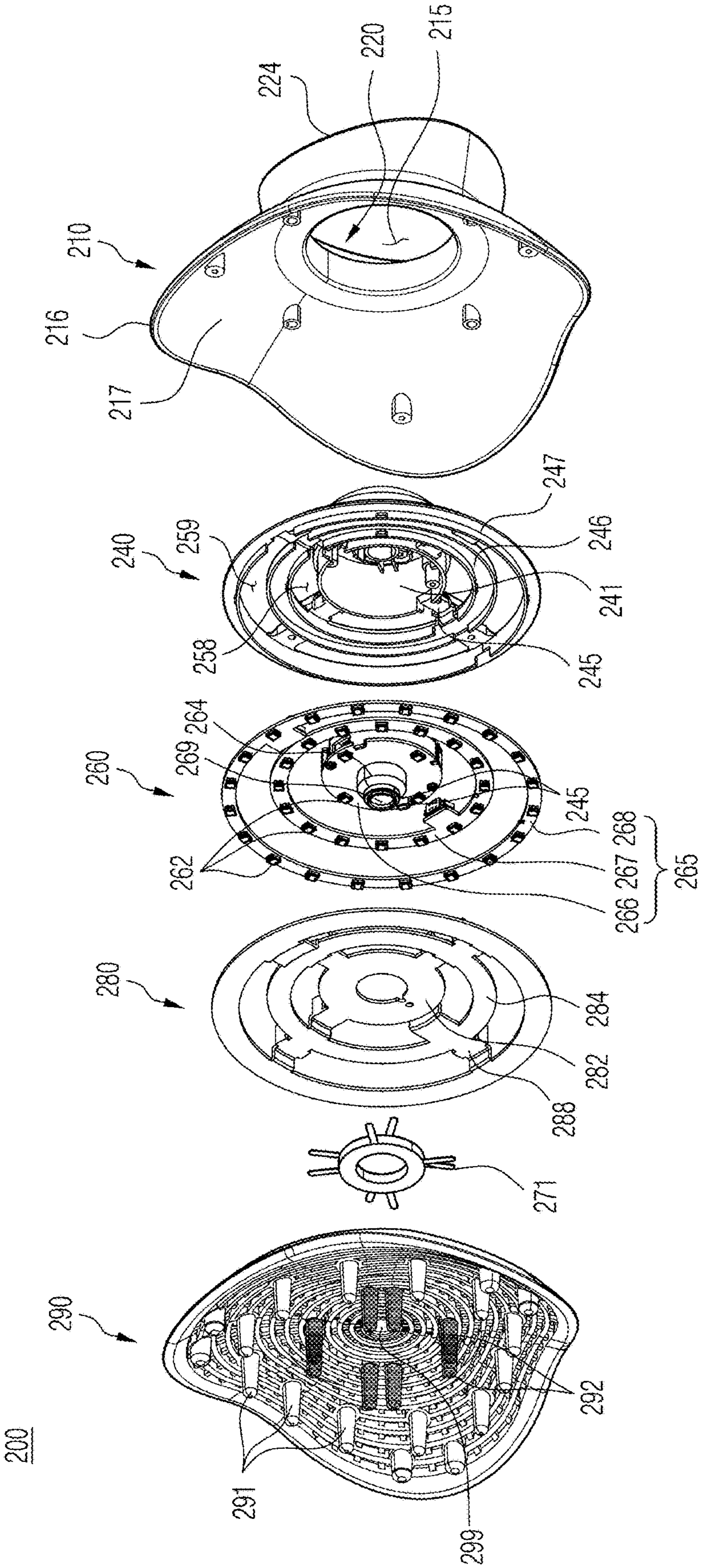
FIG. 6 is a view showing an exploded view of a diffuser according to an embodiment of the present disclosure.
Figure 7:
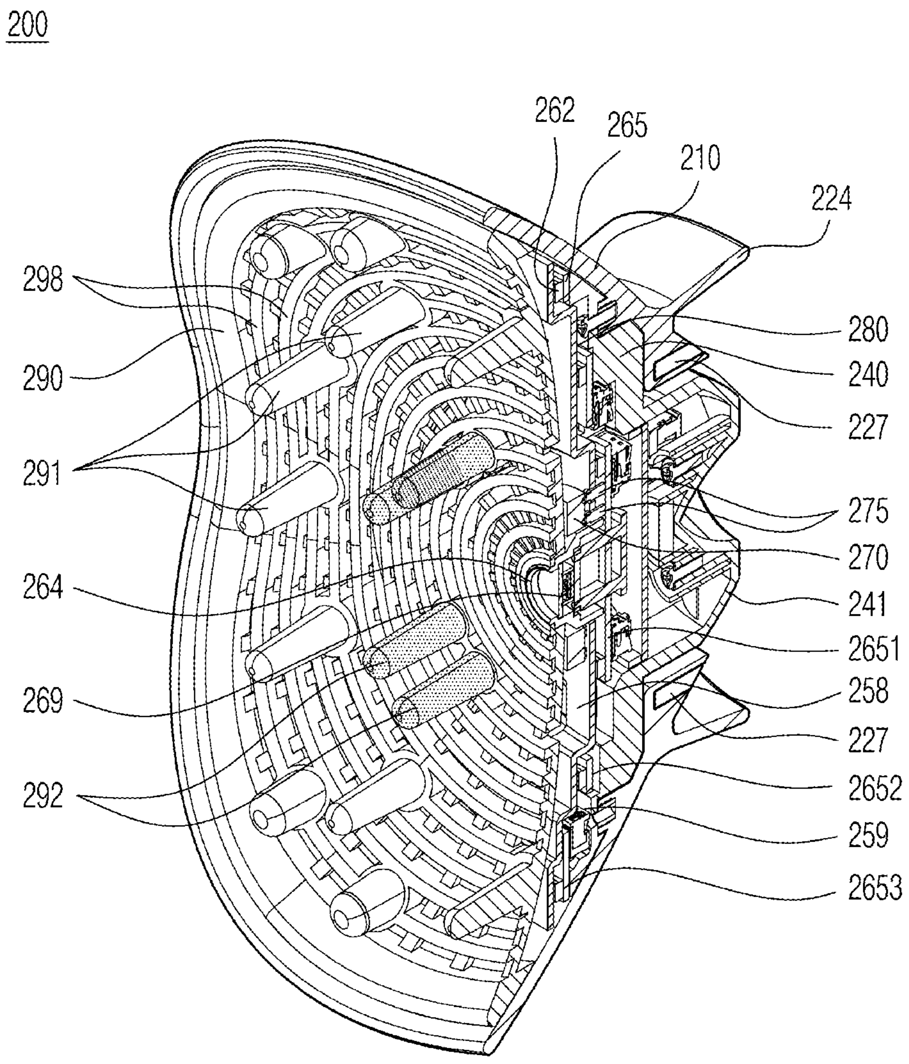
FIG. 7 is a view showing an internal cross-section of a diffuser according to an embodiment of the present disclosure.

FIG. 6 is a view showing an exploded view of the diffuser 200 according to an embodiment of the present disclosure, and FIG. 7 is a view showing an internal cross-section of the diffuser 200 according to an embodiment of the present disclosure.

Referring to FIGS. 6 and 7, the diffuser 200 according to an embodiment of the present disclosure may include the diffusing case 210, a guide frame 240, the light irradiator 260, a light diffusion frame 280, electrode connector 264, and the discharge cover 290.

In the diffusing case 210, the rear side 212 may be coupled with the main body 101, and the open surface may be defined in the front side 211. The inner diameter of the diffusing case 210 may increase from the rear side 212 to the front side 211, so that the inside gas may be diffused and discharged to the outside.

That is, the gas discharged through the gas outlet 120 of the main body 101 may be provided to the user in a state in which the flow cross-sectional area thereof is increased as the gas is flowing in the diffusing case 210.

FIGS. 6 and 7 show the diffusing case 210 in which the inner diameter thereof increases from the rear side 212 to the front side 211 and accordingly an outer diameter thereof increases in the same manner.

The gas inlet hole 185 may be defined in the rear side 212 of the diffusing case 210. When the diffusing case 210 is coupled to the main body 101, the gas inlet hole 185 is positioned to face the gas outlet 120. Further, the gas discharged from the gas outlet 120 may be introduced into the diffusing case 210 through the gas inlet hole 185.

The gas inlet hole 185 may be located at a center of the rear side 212 of the diffusing case 210 when viewed from the rear, and a cross-section shape of the gas inlet hole 185 may correspond to the gas outlet 120. For example, the gas inlet hole 185 is defined to have an inner diameter larger than the side portion 125 of the gas outlet 120, so that the gas discharged from the gas outlet 120 may be completely introduced into the diffusing case 210 through the gas inlet hole 185.

The second coupling portion 220 coupled to the main body 101 may be disposed on the rear side 212 of the diffusing case 210. The diffusing case 210 may include a rear circumferential portion 217 surrounding the gas inlet hole 185 in the rear side 212, and the second coupling portion 220 may be disposed at the rear circumferential portion 217.

The second coupling portion 220 may further include a coupling sleeve 224. The coupling sleeve 224 may extend rearward from the rear circumferential portion 217. The coupling sleeve 224 may be disposed to outwardly surround the front end 112 of the main body 101.

The second coupling portion 220 may have a second magnetic fastening portion 227 embedded in the rear circumferential portion 217 or located inside the rear circumferential portion 217, and may include a power receiver disposed on an inner surface and the like of the coupling sleeve 224.

In addition, the first coupling portion 127 may be disposed at the front end 112 of the main body 101, may have a first magnetic fastening portion 127*a* embedded inside the outer wall of the front end 112 or located inside the outer wall, and may include a power transmitter disposed on an outer surface and the like of the outer wall of the front end 112.

The first coupling portion 127 is coupled to the second coupling portion 220. At least one of the first magnetic fastening portion 127*a*, see FIG. 3, and the second magnetic fastening portion 227 may include a magnetic force generator, so that the first magnetic fastening portion 127 and the second magnetic fastening portion 227 may be magnetically coupled to each other. The magnetic coupling means a scheme of mutual coupling through a magnetic force generated from the magnetic force generator such as a magnet and an electromagnet.

The power transmitter may supply power to the power receiver in contact or connection with the power receiver. The power receiver may be connected to a component inside the diffuser 200, for example, the light irradiator 260 and the like to supply power thereto.

The open surface surrounded by the front circumferential portion 216 may be defined in the front side 211 of the diffusing case 210, and the gas inside the diffusing case 210 may be discharged forward of the diffuser 200 through the open surface in the front side 211.

In one example, the guide frame 240 may be disposed inside the diffusing case 210. The guide frame 240 is disposed to guide the flow of the gas introduced through the gas inlet hole 185.

The guide frame 240 may be disposed to face the gas inlet hole 185 of the diffusing case 210. The guide frame 240 may have a diffusion portion 241 at a center thereof, a first guide 246 disposed radially outward of the diffusion portion 241, and a second guide 247 disposed radially outward of the first guide 246.

The guide frame 240 may include a guide connector 245 extending along the radial direction of the diffuser 200, and the guide connector 245 may connect the diffusion portion 241, the first guide 246, and the second guide 247 to each other.

The diffusion portion 241 of the guide frame 240 is disposed to face the gas inlet hole 185 to diffuse the gas introduced through the gas inlet hole 185 outward in the radial direction. That is, the flow cross-sectional area of the gas introduced through the gas inlet hole 185 may be increased by the diffusion portion 241.

According to an embodiment of the present disclosure, in the gas outlet 120 having the center portion 126 and the side portion 125, a flow direction of the gas discharged from the center portion 126 may be changed by the diffusion portion 241. That is, the diffusion portion 241 may have a larger diameter than the center portion 126 and diffuse the gas provided from the center portion 126 outward in the radial direction.

The first guide 246 may have a ring shape, and the diffusion portion 241 may be located at a center of the first guide 246. The diffusion portion 241 may have a circular cross-section, and may be outwardly spaced apart from the diffusion portion 241 while being concentric with the diffusion portion 241 of the first guide 246.

A first flow path 258 may be located between the first guide 246 and the diffusion portion 241. That is, the first guide 246 may be spaced apart from the diffusion portion 241 to define the first flow path 258 between the first guide 246 and the diffusion portion 241. The gas diffused through the diffusion portion 241 may flow through the first flow path 258.

The second guide 247 may have a ring shape corresponding to the first guide 246, and the diffusion portion 241 and the first guide 246 may be located at a center of the second guide 247. That is, the second guide 247 may be concentric with the diffusion portion 241 and the first guide 246 and may be spaced apart from the first guide 246.

That is, an inner diameter of the first guide 246 may be larger than the diameter of the diffusion portion 241, and an inner diameter of the second guide 247 may be larger than an outer diameter of the first guide 246. Accordingly, the first flow path 258 may be defined between the diffusion portion 241 and the first guide 246, and a second flow path 259 may be defined between the first guide 246 and the second guide 247.

The gas diffused by the diffusion portion 241 may flow through the first flow path 258 and the second flow path 259. An outer diameter of the second flow path 259 may be larger than the diameter of the gas inlet hole 185, so that the gas introduced through the gas inlet hole 185 may be diffused by the diffusion portion 241 and flow with a larger flow cross-section.

The light irradiator 260 may be located in front of the guide frame 240. The light irradiator 260 may be installed on a front surface of the guide frame 240. The light irradiator 260 may have a plurality of light emitters 262 arranged on a circuit board 265. The circuit board 265 may include a plurality of circuit boards separated from each other, and the plurality of boards may be respectively arranged on the diffusion portion 241, the first guide 246, and the second guide 247 of the guide frame 240.

The light irradiator 260 may include the plurality of circuit boards 265, and the plurality of circuit boards 265 may respectively include a central board 2651, a first board 2652, and a second board 2653.

The central board 2651 may have a cross-section shape corresponding to the diffusion portion 241. For example, the diffusion portion 241 may have the circular cross-section, and the central board 2651 may have a circular cross-section in the same manner as the diffusion portion 241, may be disposed on a front surface of the diffusion portion 241, and may include the plurality of light emitters 262.

The light emitting unit 262 may be an LED or a low-output laser, and may supply light energy generated by combination of laser and LED light to the scalp.

The first board 2652 may have a shape corresponding to the first guide 246. For example, the first guide 246 may have the ring shape, and the first board 2652 may have a ring shape in the same manner as the first guide 246, may be disposed on a front surface of the first guide 246, and may include the plurality of light emitters 262.

The second board 2653 may have a shape corresponding to the second guide 247. For example, the second guide 247 may have the ring shape, and the second board 2653 may have a ring shape in the same manner as the second guide 247, may be disposed on a front surface of the second guide 247, and may include the plurality of light emitters 262.

The central board 2651, the first board 2652, and the second board 2653 may be arranged to be concentric like the guide frame 240. The first board 2652 may be outwardly spaced apart from the central board 2651, and the second board 2653 may be outwardly spaced apart from the first board 2652.

That is, an inner diameter of the first board 2652 may be larger than a diameter of the central board 2651, and an inner diameter of the second board 2653 may be larger than an outer diameter of the first board 2652. Therefore, like the guide frame 240, the first flow path 258 may be located between the central board 2651 and the first board 2652, and the second flow path 259 may be located between the first board 2652 and the second board 2653.

The light irradiator 260 may irradiate light toward the front side 211 of the diffusing case 210 through the plurality of light emitters 262. The light irradiated from the light irradiator 260 may be provided to a location ahead of the diffuser 200 through the front side 211 of the diffusing case 210.

For example, the light irradiated from the light irradiator 260 may be provided to the location ahead of the diffuser 200 by passing through the open surface of the diffusing case 210, passing through the gas discharge hole 298 of the discharge cover 290, passing through the discharge cover 290, or passing through the massage protrusion 291 of the discharge cover 290.

As the light is irradiated to the location ahead of the diffuser 200, the diffuser 200 according to an embodiment of the present disclosure may perform user's hair or scalp care. The light irradiated from the light irradiator 260 may contribute to improving scalp and hair health while drying the user's scalp or hair or providing heat to the user's scalp or hair.

In particular, light energy provided by the light irradiator 260 may be absorbed by hair follicle cells, may activate cell metabolism and help to supply nutrients, which can help treat hair loss.

The proximity sensor 269 may be disposed on the circuit board 265 of the light irradiator 260. FIG. 6 shows a state in which the proximity sensor 269 is disposed on the central board 2651 of the light irradiator 260 according to an embodiment of the present disclosure.

The proximity sensor 269 may be disposed at a center of the central board 2651. The proximity sensor 269 may be disposed to measure the separation distance from the target positioned in front of the proximity sensor 269. The controller 130 may be disposed to control the light irradiator 260 based on the separation distance between the proximity sensor 269 and the front target measured by the proximity sensor 269.

For example, when the separation distance from the target measured by the proximity sensor 269 is equal to or less than a reference distance, the controller 130 may control the light irradiator 260 such that the light irradiator 260 irradiates the light forward. The reference distance may be predetermined in terms of a design or control.

However, the light irradiator 260 may be operated through a physical switch that is operated when the separation distance measured by the proximity sensor 269 is equal to or less than the reference distance.

In an embodiment of the present disclosure, as the proximity sensor 269 is used, the light irradiator 260 is operated when the separation distance from the target in front of the diffuser 200, for example, the scalp or the hair of the user is equal to or less than the reference distance, thereby improving ease of use and an operation efficiency.

The proximity sensor 269 may be disposed in various types. For example, the proximity sensor 269 may be a pressure sensor that detects whether a pressing force is applied from the user's scalp or hair, or a photosensitive sensor that measures a level at which an amount of sensed light decreases as the separation distance from the scalp or the hair decreases.

In addition, the proximity sensor 269 may be an IR sensor that measures an infrared ray transmitted from the front target, that is, the user's scalp or hair to measure the separation distance from the scalp or the hair. In this case, the proximity sensor 269 may be disposed to irradiate the infrared ray forward.

In one example, the light diffusion frame 280 may be located in front of the light irradiator 260. The light diffusion frame 280 may be installed on a front surface of the light irradiator 260. That is, the light diffusion frame 280 may be disposed to forwardly cover the light irradiator 260.

The light diffusion frame 280 may include a central light diffusion portion 282, a first light diffusion portion 284 and a second light diffusion portion 286. The light diffusion frame 280 may further include a light diffusion connector 288 for connecting the central light diffusion portion 282, the first light diffusion portion 284, and the second light diffusion portion 286 to each other.

The central light diffusion portion 282 may have a cross-section shape corresponding to the central board 2651. For example, the central board 2651 may have the circular cross-section, and the central light diffusion portion 282 may have a circular cross-section in the same manner as the central board 2651 and may cover the front surface of the diffusion portion 241.

The first light diffusion portion 284 may have a shape corresponding to the first board 2652. For example, the first board 2652 may have the ring shape, and the first light diffusion portion 284 may have a ring shape in the same manner as the first board 2652 and may cover the front surface of the first board 2652.

The second light diffusion portion 286 may have a shape corresponding to the second board 2653. For example, the second board 2653 may have the ring shape, and the second light diffusion portion 286 may have a ring shape in the same manner as the second board 2653 and may cover the front surface of the second board 2653.

The central light diffusion portion 282, the first light diffusion portion 284, and the second light diffusion portion 286 may be arranged to be concentric like the guide frame 240 and the light irradiator 260. The first light diffusion portion 284 may be outwardly spaced apart from the central light diffusion portion 282, and the second light diffusion portion 286 may be outwardly spaced apart from the first light diffusion portion 284.

That is, an inner diameter of the first light diffusion portion 284 may be larger than a diameter of the central light diffusion portion 282, and an inner diameter of the second light diffusion portion 286 may be larger than an outer diameter of the first light diffusion portion 284. Accordingly, like the guide frame 240, the first flow path 258 may be located between the central light diffusion portion 282 and the first light diffusion portion 284, and the second flow path 259 may be located between the first light diffusion portion 284 and the second light diffusion portion 286.

That is, the diffuser 200 according to an embodiment of the present disclosure may be disposed in a shape in which the first flow path 258 and the second flow path 259 are extended in the front and rear direction through the guide frame 240, the light irradiator 260, and the light diffusion frame 280.

The light diffusion connector 288 may be disposed in a shape corresponding to the guide connector 245. For example, the guide connector 245 and the light diffusion connector 288 may have an extended shape along the radial direction of the diffuser 200.

The light diffusion connector 288 may be located in front of the guide connector 245. The light diffusion frame 280 may be fixed inside the diffusing case 210 as the light diffusion frame 280 is fastened to the guide connector 245.

An embodiment of the present disclosure is advantageous in terms of a design and structurally stable in that, in a state in which the guide frame 240 is constituted by a plurality of components, the plurality of components are able to be handled as a single component through the guide connector 245.

In addition, an embodiment of the present disclosure is advantageous in terms of the design and structurally stable in that, in a state in which the light diffusion frame 280 is constituted by a plurality of components, the plurality of components are able to be handled as a single component through the light diffusion connector 288.

Furthermore, the light diffusion connector 288 of the light diffusion frame 280 is coupled to the guide connector 245 of the guide frame 240, so that all of the central light diffusion portion 282, the first light diffusion portion 284, and the second light diffusion portion 286 may be stably fixed, which is advantageous in terms of coupling.

The light diffusion frame 280 may be made of a material through which light is transmitted. For example, the light diffusion frame 280 may be made of a transparent or translucent material. The light irradiated from the light irradiator 260 may be scattered and diffused while passing through the light diffusion frame 280.

In the diffuser 200 according to an embodiment of the present disclosure, the light diffusion frame 280 is disposed in front of the light irradiator 260, so that the light irradiated from the light irradiator 260 may be provided to the user while being scattered and diffused and being uniformly dispersed in a larger area.

A treatment for the diffusion or the scattering of the light may be performed on a front surface or a back surface of the light diffusion frame 280. For example, etching may be performed or a pattern through laser processing and the like may be formed on a surface of the light diffusion frame 280.

In one example, the central light diffusion portion 282 is disposed to shield the front surface of the central board 2651, and a portion of the central light diffusion portion 282 in front of the proximity sensor 269 may be opened such that the measurement of the separation distance from the target in front of the diffuser 200 by the proximity sensor 269 disposed on the central board 2651 is easy.

FIG. 6 shows a state in which the proximity sensor 269 is disposed at the center of the central board 2651 according to an embodiment of the present disclosure and the central light diffusion portion 282 has a hole defined at a center thereof to expose the proximity sensor 269 forwardly.

The discharge cover 290 may be disposed to shield the open surface defined in the front side 211 of the diffusing case 210 in which the guide frame 240, the light irradiator 260, and the light diffusion frame 280 are embedded. The plurality of gas discharge holes 298 are defined in the discharge cover 290, so that the gas may be discharged and the light may be irradiated forward.

The discharge cover 290 may be disposed such that the edge 297 has a curvature to correspond to the front circumferential portion 216 of the diffusing case 210 when viewed from the side and is indented rearwards centerwardly when viewed from the front.

That is, a front surface of the discharge cover 290 may form a curved surface that is indented rearwards centerwardly, so that the discharge cover 290 may have a shape corresponding to the head of the user and may be optimized to provide the massage effect through the massage protrusion 291 while providing the gas and the light to the user.

The plurality of massage protrusions 291 protruding or extending forward on the front surface of the discharge cover 290 may be arranged. The massage protrusions 291 may be made of the same plastic material as the discharge cover 290. A contact portion may be disposed on the surface of the discharge cover 290 such that a sense of touch with the scalp or the hair of the user may be improved and damage to the scalp and the hair may be minimized. The contact portion may be made of a material such as silicon and the like.

Some of the plurality of massage protrusions 291 may correspond to the iontophoresis electrode 292.

The iontophoresis module 270 may generate a microcurrent to care for the scalp. When a weak current flows to the skin, charges may enable materials on the scalp to penetrate deep into the scalp layer, thereby improving the scalp health and increasing the regenerative effect.

The iontophoresis module 270 is made of a metal material to allow current to flow therein, and may penetrate the discharge cover 290 and protrude toward a back surface of the discharge cover 290. That is, the front end of the iontophoresis module 270 is in contact with the scalp, and the rear end of the iontophoresis module 270 is connected to the electrode connector 271 which will be described later.

The iontophoresis module 270 may include a plurality of iontophoresis electrodes 292 located on the discharge cover 290 to contact the scalp. The iontophoresis electrodes 292 may consist of a pair of electrodes connected to different poles, and may include a plurality of pairs of iontophoresis electrodes 292, as shown in FIG. 5.

Figure 10:
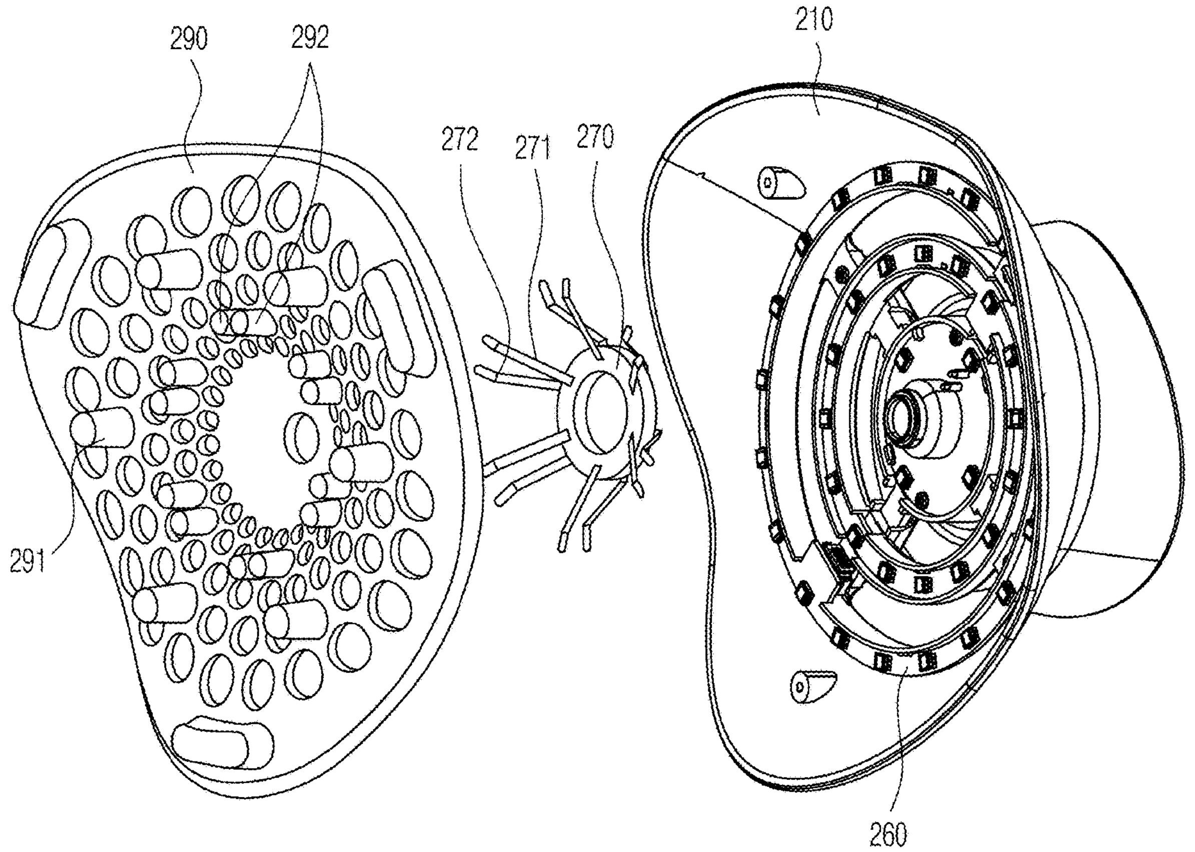
FIG. 10 is an exploded view illustrating a diffuser according to another embodiment of the present disclosure.

The present embodiment illustrates an example in which the iontophoresis module 270 includes four pairs of iontophoresis electrodes 292, and more electrodes may be provided as in the embodiment shown in FIG. 10.

In the present embodiment, the iontophoresis electrodes 292 may be arranged at equal intervals in the circumferential direction to uniformly exert the iontophoresis effect on the scalp. In the present embodiment, the iontophoresis electrodes 292 may be shown to be located at the same distance from the center of the discharge cover 290 for convenience of description, but the scope or spirit of the present disclosure is not limited thereto. Alternatively, the iontophoresis electrodes 292 may also be placed at different locations as necessary. The iontophoresis electrodes 292 may be disposed to measure the moisture amount of the scalp or the hair of the user. A pair of the iontophoresis electrodes 292 may be arranged to measure an impedance.

The iontophoresis electrodes 292 must be connected to the controller 130 to apply a current to the scalp. Since the circuit board 265 of the light irradiator 260 is connected to the controller 130 and supplies power to the light emitting unit 262, the iontophoresis electrodes 292 may receive a power-supply voltage using the circuit board 265 of the light irradiator 260.

For connection between the circuit board 265 and the iontophoresis electrodes 292, the circuit board 265 and the iontophoresis electrodes 292 are fastened to each other in a pin lock structure. For cable soldering, etc., it is difficult to release such connection between the circuit board 265 and the iontophoresis electrodes 292. If the detachable connector structure such as the pin lock structure is long, it is difficult to handle wires or cables, and if the detachable connector structure is short, it is difficult for the user to separate the connector structure.

In particular, in a state in which the plurality of iontophoresis electrodes 292 is individually connected to the hair dryer, when the user desires to separate the iontophoresis electrodes 292 from the hair dryer, the user must disconnect all of the electrodes from each other, resulting in user inconvenience. Additionally, the discharge cover 290 must be fastened to the diffusing case 210 at a predetermined angle and cannot be connected to rotate around the center of an axis thereof.

Accordingly, in the present embodiment, the iontophoresis electrodes 292 and the circuit board 265 can be connected to each other using the electrode connector 271 that includes the pogo pin 275 and the elastic leaf spring terminals 2721 and 2731.

Figure 8:
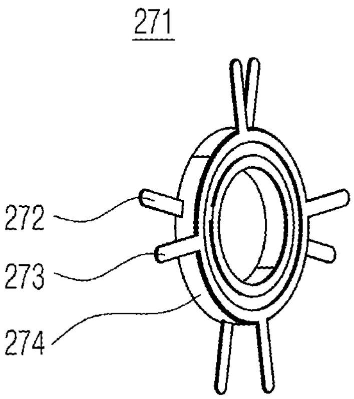
FIG. 8 is a perspective view and an exploded view illustrating an electrode connector according to an embodiment of the present disclosure.
Figure 8:
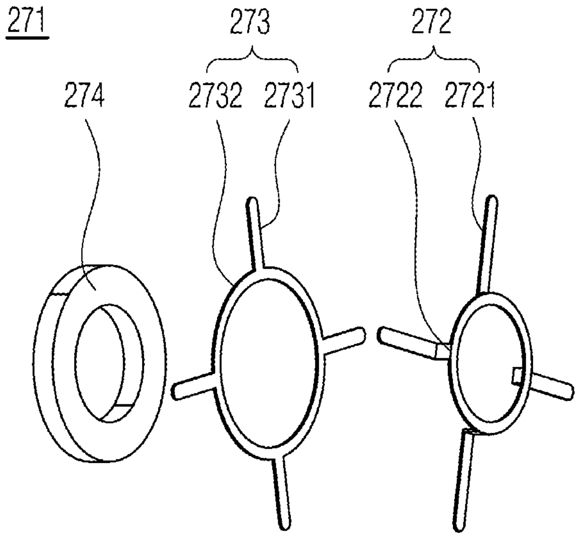

FIG. 8 is a perspective view and an exploded view illustrating the electrode connector 271 according to an embodiment of the present disclosure.

The pogo pin 275 protruding from the circuit board 265 may be an elastic terminal, and any elastic terminal such as a C clip other than the pogo pin 275 can be applied to the electrode connector 271. The pogo pin 275 may be located on the central board 2651 located at the center of the circuit board 265.

The electrode connector 271 may include a ring-shaped connection frame 274, a first connection electrode 272 connected to the first pole, and a second connection electrode 273 connected to the second pole. Each of the first pole and the second pole may have any one of a positive(+) pole and a negative(−) pole, and the first pole and the second pole may operate as opposite poles.

The connection frame 274 may include an opening at the center thereof so that the proximity sensor can be placed in the opening. The connection frame 274 may be formed in a ring shape, so that the ring-shaped connection frame 274 can overlap the pogo pin 275 of the circuit board 265 regardless of the coupling direction of the discharge cover 290.

The first connection electrode 272 may include a ring electrode 2722 that has a ring shape along the connection frame 274, and a plurality of branch electrodes 2721 extending from the ring electrodes 2722. The second connection electrode 273 may include a ring electrode 2732 that has a ring shape along the connection frame 274, and a plurality of branch electrodes 2731 extending from the ring electrode 2732. Each of the branch electrodes (2721, 2731) may be formed to protrude from the connection frame 274.

The number of branch electrodes (2721, 2731) may correspond to the number of iontophoresis electrodes 292. That is, since four pairs of iontophoresis electrodes 293 are provided in the electrode connector 271, the number of the branch electrodes 2721 of the first connection electrode 272 is four, the number of the branch electrodes 2731 of the first connection electrode 272 is four, the number of the branch electrodes 2721 of the second connection electrode 273 is four, and the number of the branch electrodes 2731 of the second connection electrode 273 is four. The ends of branch electrodes (2721, 2731) may be connected to the iontophoresis electrode 292.

The first ring electrode 2722 and the second ring electrode 2732 have different sizes and are disposed at different positions on the connection frame 274 so that they do not overlap each other. The first ring electrode 2722 and the second ring electrode 2732 may be exposed in the backward direction of the connection frame 274 so that the first ring electrode 2722 and the second ring electrode 2732 can be connected to the pogo pin 275. The first ring electrode 2722 and the second ring electrode 2732 may form concentric circles having different diameters as shown in FIG. 8.

The first ring electrode 2722 is located inside the second ring electrode 2732. When the branch electrodes (2721, 2731) of the first connection electrode 272 extend on the same plane as the ring electrodes (2722, 2732), the branch electrodes (2721, 2731) may overlap the second ring electrode 2732. As a result, as shown in FIG. 8(*b*), the first ring electrode 2722 can be configured to extend radially after being bent in the forward direction from the first ring electrode 2722.

When the first connection electrode 272 and the second connection electrode 273 are placed and the connection frame 274 is injection-molded, the branch electrodes (2721, 2731) of the first connection electrode 272 may be formed to protrude radially from the side direction of the connection frame 274 as shown in FIG. 8(*a*).

The branch electrodes (2721, 2731) of the first connection electrode 272 and the branch electrodes (2721, 2731) of the second connection electrode 273 are made of metal and have elasticity, and they may be deformed within a predetermined range, so that the connection state of the electrodes can be maintained even if the discharge cover 290 is misaligned.

Figure 9:
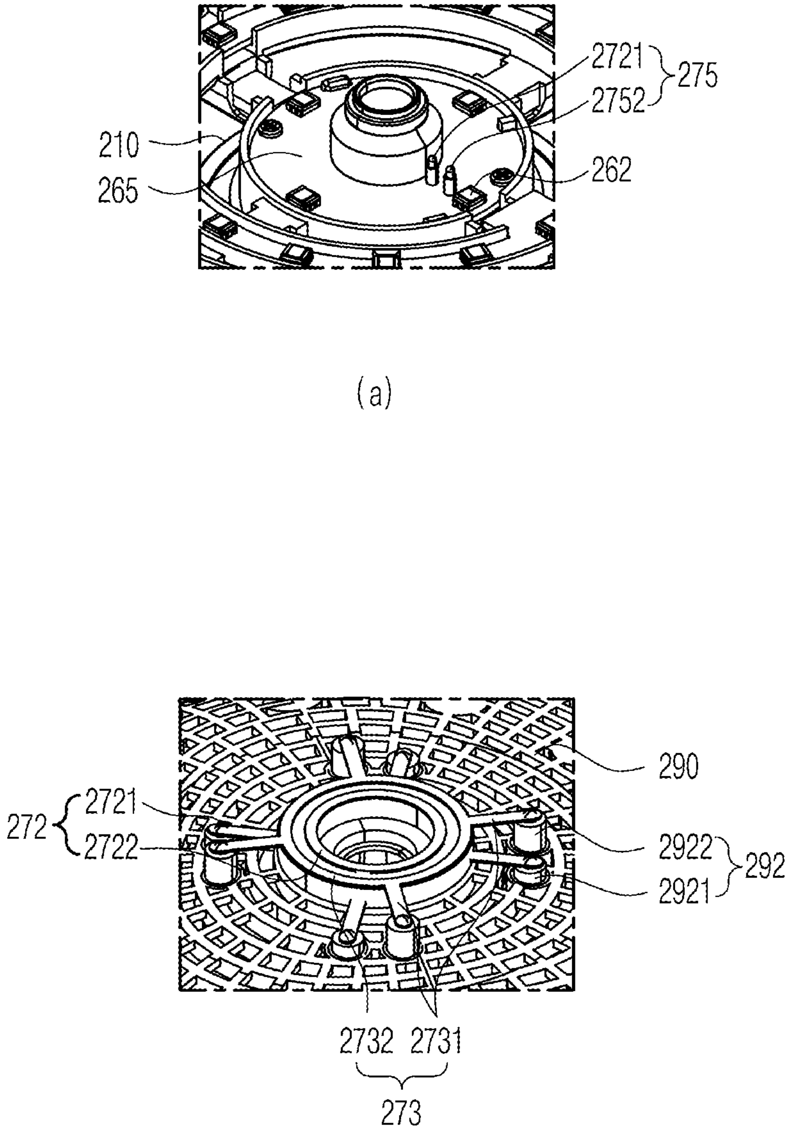
FIG. 9 is a diagram illustrating how the electrode connector connects the iontophoresis electrodes and the pogo pins according to an embodiment of the present disclosure.

FIG. 9 is a diagram illustrating how the electrode connector 271 connects the iontophoresis electrodes 292 and the pogo pins 275 according to an embodiment of the present disclosure. FIG. 9(*a*) is an enlarged view of the pogo pins 275, and FIG. 9(*b*) is a view illustrating a state in which the electrode connector 271 is coupled to the back surface of the discharge cover 290.

The pogo pins 275 may include the first pogo pin 2751 and the second pogo pin 2752 that are paired with each other. The first pogo pin 2751 and the second pogo pin 2752 are spaced apart from each other at different positions from the center of the central substrate 2651, and may be connected to different poles. The pogo pins 275 may be connected to the ring electrodes (2722, 2732) of the connection electrodes (272, 273), the first pogo pin 2751 may be connected to the first ring electrode 2722, and the second pogo pin 2752 may be connected to the second ring electrode 2732.

Although the ring electrodes (2722, 2732) are arranged side by side in the drawing, since each of the ring electrodes (2722, 2732) has a ring shape, the pair of pogo pins (2751, 2752) need not necessarily be arranged side by side in so far as their separation distances from the center of the central substrate 2651 correspond to the positions of the ring electrodes (2722, 2732). The branch electrodes (2721, 2731) of the electrode connector 271 may be connected to the iontophoresis electrode 292. The iontophoresis electrodes 292 may include the first iontophoresis electrode 2921 and the second iontophoresis electrode 2922 that are connected to different poles, and may be connected to different connection electrodes (272, 273).

In the present embodiment, the first iontophoresis electrode 2921 and the branch electrodes (2721, 2731) of the first connection electrode 272 may be connected to each other, and the second iontophoresis electrode 2922 and the branch electrodes (2721, 2731) of the second connection electrode 273 may be connected to each other.

As shown in FIG. 8, the positions of the branch electrodes (2721, 2731) of the first connection electrode 272 and the positions of the branch electrodes (2721, 2731) of the second connection electrode 273 are different from each other in the forward and backward directions, so that the length protruding toward the back surface of the discharge cover 290 of the first iontophoresis electrode 2921 may be different from the length protruding toward the back surface of the discharge cover 290 of the second iontophoresis electrode 2922. According to the present embodiment, the back-surface length of the first iontophoresis electrode 2921 is shorter than the back-surface length of the second iontophoresis electrode 2922.

FIG. 10 is an exploded view illustrating the diffuser 200 according to another embodiment of the present disclosure. Referring to FIG. 10, if the center of the discharge cover 290 is formed to have a concave shape or if there are many more iontophoresis electrodes 292, the shape of the connection electrodes (272, 273) of the electrode connector 271 may be modified and applied to the diffuser 200.

The branch electrodes (2721, 2731) may be further bent in the forward direction, and the number of branch electrodes (2721, 2731) can be further increased depending on the number of iontophoresis electrodes 292.

Further, the controller 130 may determine the impedance using a voltage, a current, a resistance, and the like, which are identified through the iontophoresis electrode 292, determine the moisture amount of the scalp or the hair of the user based on the determined impedance, and control an operation of the fan 170, the temperature adjuster 160, or the light irradiator 260 based on the determined moisture amount.

For example, the controller 130 may control the fan 170 such that the gas speed increases as the moisture amount of the scalp or the hair of the user increases, control the temperature adjuster 160 such that the gas temperature increases, or control the light irradiator 260 such that the light amount increases.

The proximity sensor 269 may be exposed forward through the hole defined in the light diffusion frame 280 and the open region 299 at a center of the discharge cover 290, and may wholly measure the separation distance from the target in front of the diffuser 200. A protection member that protects the proximity sensor 269 and allows the infrared ray or the like to pass straight therethrough may be disposed in front of the proximity sensor 269.

In an embodiment of the present disclosure, the first coupling portion 127 of the main body 101 may include the first magnetic fastening portion 127*a* (see FIG. 3) and the second coupling portion 220 of the diffuser 200 may include the second magnetic fastening portion 227 (see FIG. 7).

The diffuser 200 may be coupled to the front end 112 of the main body 101 through the magnetic coupling between the first magnetic fastening portion 127 and the second magnetic fastening portion 227. The first coupling portion 127 may further include a hook fastener and the second coupling portion 220 may further include a hook fastened to the hook fastener, so that a coupling stability between the diffuser 200 and the main body 101 may be enhanced.

Hereinafter, the flow of the gas discharged from the gas outlet 120 according to an embodiment of the present disclosure will be described with reference to FIG. 7.

In the gas outlet 120, the gas is discharged from the center portion 126 and the side portion 125. The gas inlet hole 185 of the diffusing case 210 is defined to have a diameter equal to or larger than that of the side portion 125 and face the gas outlet 120, so that the gas discharged from the center portion 126 and the side portion 125 may be introduced into the inlet hole 185.

The guide frame 240 may be disposed inside the diffusing case 210 to face the gas outlet 120. Specifically, the diffusion portion 241 of the guide frame 240 may be positioned to face the center portion 126 of the gas outlet 120.

The gas discharged from the center portion 126 flows toward the diffusion portion 241. As the diffusion portion 241 has a diameter larger than that of the center portion 126, the gas discharged from the center portion 126 may be diffused along the radial direction of the diffuser 200.

The diffusion portion 241 may have a diffusion protrusion 242 on a back surface thereof facing the center portion 126, and the diffusion effect of the gas discharged from the center portion 126 may be improved by the diffusion protrusion 242. The diffusion protrusion 242 may be disposed to increase in rearwardly protruding height toward a center on the cross-section when viewed from the rear.

At least a portion of the gas discharged from the center portion 126 may flow along the first flow path 258 defined between the diffusion portion 241 and the first guide 246 in the guide frame 240 by the diffusion portion 241 and the diffusion protrusion 242.

In one example, the gas discharged from the side portion 125 may have a flow form outwardly surrounding the gas discharged from the center portion 126, and the gas discharged from the side portion 125 may also diffuse outward along the radial direction of the diffuser 200 as the gas of the center portion 126 is diffused by the diffusion portion 241.

Therefore, at least a portion of the gas discharged from the side portion 125 and at least a portion of the gas discharged from the center portion 126 may flow along the second flow path 259 defined between the first guide 246 and the second guide 247 in the guide frame 240.

In an embodiment of the present disclosure, despite a design feature that the inner diameter of the diffuser 200 increases forwardly, the discharging of the gas discharged from the center portion 126 and the side portion 125 in the forward direction while being maintained in a specific form may be effectively suppressed through the guide frame 240.

Furthermore, in an embodiment of the present disclosure, the diffuser 200 allows the gas discharged from the center portion 126 and the side portion 125 to be effectively dispersed and diffused with a larger flow cross-sectional area while preventing the flow of the gas from being maintained in the specific form.

In one example, the light irradiator 260 and the light diffusion frame 280 may be arranged in front of the guide frame 240 inside the diffusing case 210. The light irradiator 260 and the light diffusion frame 280 may be coupled with the guide frame 240 and thus may be handled as a single component, so that a structure that is excellent in a space utilization and is advantageous in design may be implemented.

In addition, the light irradiator 260 and the light diffusion frame 280 may define the first flow path 258 and the second flow path 259 together with the guide frame 240. In an embodiment of the present disclosure, as the structure in which the light irradiator 260 and the light diffusion frame 280 define the first flow path 258 and the second flow path 259 together with the guide frame 240 is achieved, the flow of the gas formed by the guide frame 240 may be effectively maintained and the gas may be discharged forwardly of the diffuser 200 through the light irradiator 260 and the light diffusion frame 280.

In one example, in the light irradiator 260, the first board 2652 may be positioned forwardly of the central board 2651, and the second board 2653 may be positioned forwardly of the first board 2652. Accordingly, the plurality of light emitters 262 arranged in the light irradiator 260 may be arranged to form a spherical surface that is substantially indented rearward.

Accordingly, the plurality of light emitters 262 may be arranged in a form in which a distance from a center of the light irradiator 260 along the radial direction increases forwardly. Such arrangement of the light emitters 262 may correspond to the shape of the front surface of the discharge cover 290 indented rearward.

That is, in an embodiment of the present disclosure, the plurality of light emitters 262 arranged on the light irradiator 260 are arranged to form the curved surface to correspond to the user's head having the curvature, so that a uniform amount of light may be provided to the user's scalp and hair.

Like the light irradiator 260, the guide frame 240 may be disposed such that the first guide 246 is positioned forwardly of the diffusion portion 241 and the second guide 247 is positioned forwardly of the first guide 246.

Accordingly, the first board 2652 disposed on the front surface of the first guide 246 may be positioned forwardly of the central board 2651 disposed on the front surface of the diffusion portion 241, and the second board 2653 disposed on the front surface of the second guide 247 may be positioned forwardly of the first board 2652.

Like the light irradiator 260, in the light diffusion frame 280, the first light diffusion portion 284 may be positioned forwardly of the central light diffusion portion 282 and the second light diffusion portion 286 may be positioned forwardly of the first light diffusion portion 284. Accordingly, a distance between the light diffusion frame 280 and the light irradiator 260 may be kept constant, and uniform dispersion and scattering of the light may be induced.

In addition, in the guide frame 240, as the second guide 247 is positioned forwardly of the first guide 246 and the first guide 246 is positioned forwardly of the diffusion portion 241, a space in which the gas introduced from the gas inlet hole 185 is diffused in the radial direction may be secured and the gas may be smoothly introduced into the first flow path 258 and the second flow path 259.

FIG. 7 shows the guide frame 240, the light irradiator 260, and the light diffusion frame 280 protruding forward in a direction away from centers thereof, according to an embodiment of the present disclosure.

In one example, FIG. 7 shows a light blocking portion 264 surrounding the proximity sensor 269. The light blocking portion 264 may be disposed to surround the proximity sensor 269 along the circumferential direction of the diffuser 200, thereby preventing a situation in which the light emitter 262 around the proximity sensor 269 affects the proximity sensor 269.

In addition, the light blocking portion 264 may be opened forward to prevent structural interference from occurring in a measurement of the separation distance between the diffuser 200 and the front target by the proximity sensor 269. For example, when the proximity sensor 269 measures the infrared ray transmitted from the target, the light blocking portion 264 is opened forward to allow the infrared ray transmitted from the target to be completely provided to the proximity sensor 269.

The light blocking portion 264 may be formed in a hollow cylindrical shape. The proximity sensor 269 may be located inside the light blocking portion 264. The light blocking portion 264 may have a shape extending from the central board 2651 to the discharge cover 290.

The light blocking portion 264 may be disposed to extend rearward from the discharge cover 290, or may be formed integrally with the discharge cover 290 or integrally with the central board 2651. The light blocking portion 264 may be manufactured separately from the discharge cover 290 and the central board 2651, and may be coupled or connected to the discharge cover 290 and/or the central board 2651.

In one example, as described above, the hair dryer 100 according to an embodiment of the present disclosure includes the main body 101, the handle 102, and the diffuser 200, and the diffuser 200 includes the diffusing case 210 and the discharge cover 290.

FIG. 8 shows a view of the diffuser 200 according to an embodiment of the present disclosure viewed from the front. Referring to FIG. 8, in an embodiment of the present disclosure, the discharge cover 290 may include the plurality of massage protrusions 291.

The plurality of massage protrusions 291 may protrude forward to press the target located in front of the discharge cover 290. In addition, the plurality of massage protrusions 291 may include the iontophoresis electrode 292. The iontophoresis electrode 292 may be disposed to measure the moisture amount of the target.

Specifically, in an embodiment of the present disclosure, the massage protrusion 291 may be disposed on the discharge cover 290, and may include the plurality of massage protrusions to press the front target, for example, the scalp, the hair, or the like of the user.

The massage protrusion 291 may have a shape of a protrusion protruding forward from the discharge cover 290, and a shape of a cross-section thereof may be various, such as circular or polygonal. A protrusion length of the massage protrusion 291 may vary in design.

For example, the plurality of massage protrusions 291 arranged on the discharge cover 290 may have the same protrusion length in an entire range of the discharge cover 290. Alternatively, a massage protrusion 291 disposed in a specific region may have a larger protrusion length than a massage protrusion 291 disposed in a remaining region.

The massage protrusion 291 may further include a contact cover forming a surface of the massage protrusion 291 to minimize damage to the user's scalp and hair. The contact cover may be made of a material, such as silicone, that may minimize the damage to the scalp and hair due to friction and the like.

Light emitted from the light emitting unit 262 may be transmitted to the massage projection 291 through the gas discharge hole 298, or the discharge cover 290 may be made of a light-transmissive material so that the light can be transferred to the massage projection 291.

Figure 11:
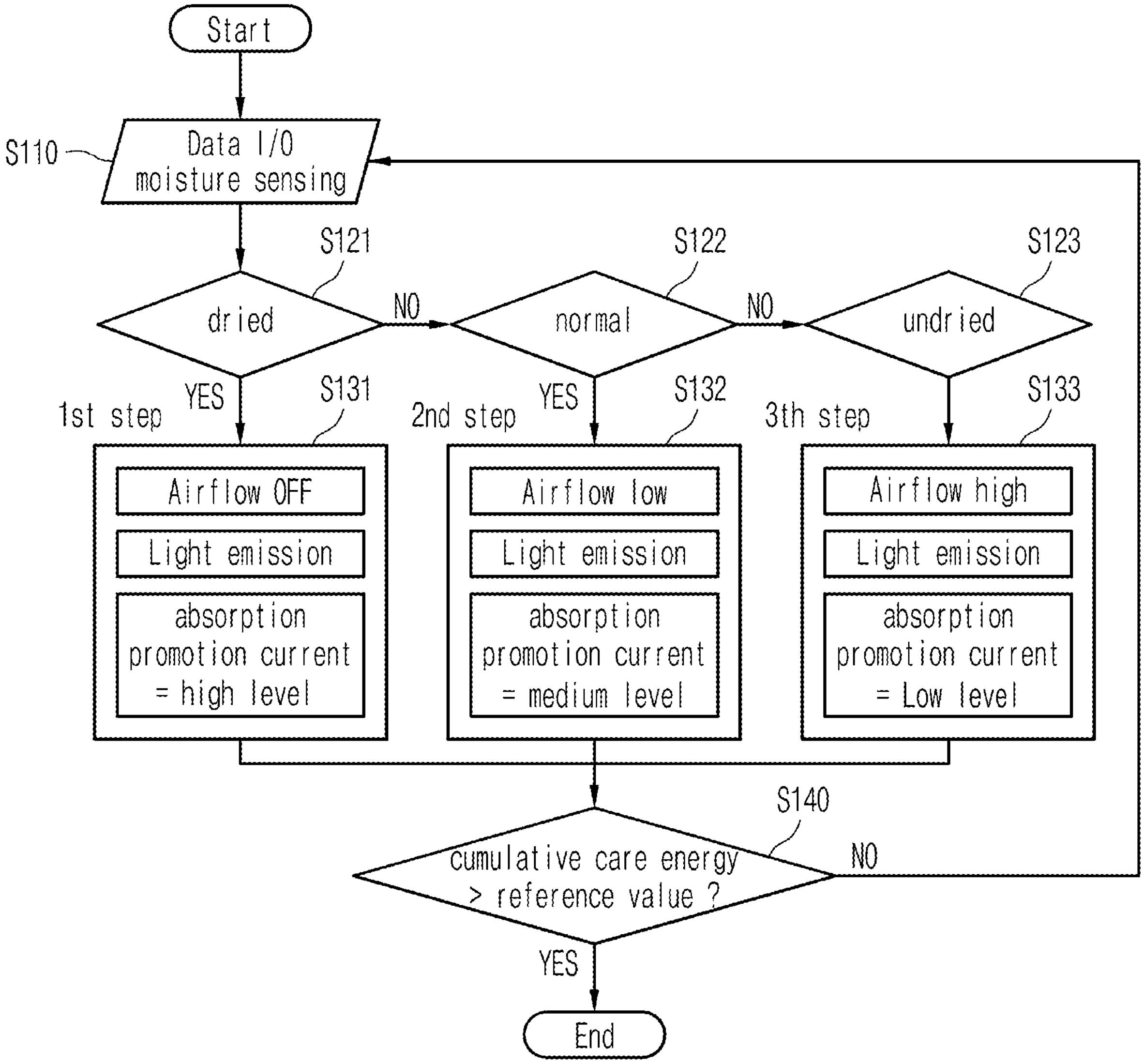
FIG. 11 is a flowchart illustrating a method for controlling a hair dryer according to an embodiment of the present disclosure.

FIG. 11 is a flowchart illustrating a method for controlling the hair dryer 100 according to an embodiment of the present disclosure. Referring to FIG. 11, the moisture of the scalp can be sensed using the iontophoresis electrode 292 (S110).

If the sensed moisture is within a normal range, it can be determined that the scalp is in a normal state (S122). If the sensed moisture is less than the normal range, it can be determined that the hair and scalp are in a dried state (S121). If the sensed moisture is equal to or greater than the normal range, it can be determined that the hair and scalp are in an undried state (S123). If the hair and scalp are in the undried state, drying of the scalp must be performed, so that the fan unit 170 can be controlled to maximize the air volume from the hair dryer. At this time, in order to increase the drying speed, the temperature adjuster 160 can be activated to increase the temperature of the airflow.

However, if the diffuser 200 is activated at a high temperature while in contact with the head, there is a risk of burns. As a result, only when the proximity sensor detects movement of the diffuser 200 that moves away from the scalp, the diffuser 200 may operate at high temperatures, and when the proximity sensor does not detect such movement of the diffuser 200, strong cold air is supplied to the scalp and drying of the scalp can be performed.

Instead, the drying effect can be increased by operating the light irradiator 260, and at the same time the scalp care can also be performed. The effect of stimulating the scalp by light emitted from the light irradiator 260 is not directly related to the amount of moisture. However, if cumulative care energy is considered excessive, such excessive care energy may destroy the cells through excessive activation of the cells, so that the amount of light to be supplied from the light irradiator 260 can be managed to be less than or equal to the reference cumulative care energy.

Figure 12:
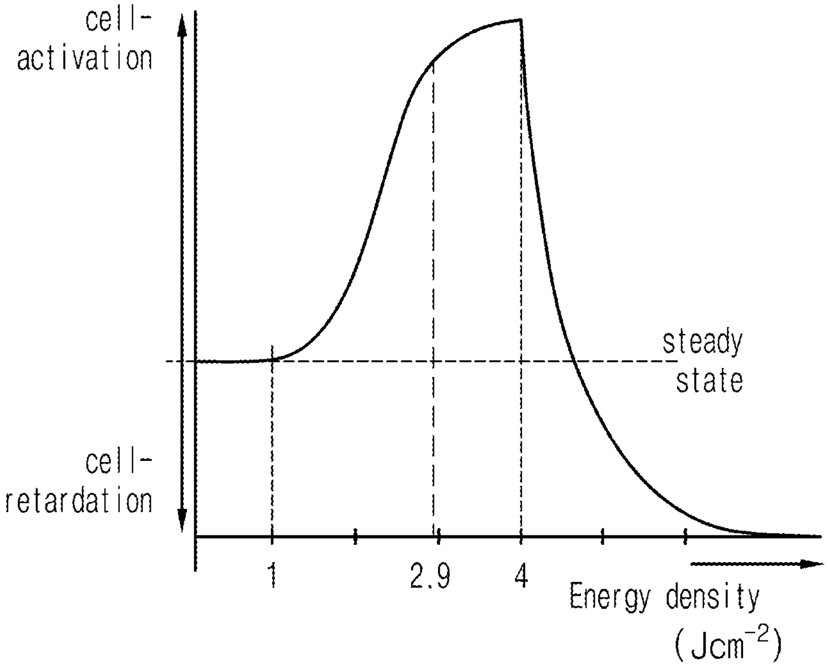
FIG. 12 is an Arndt-Schultz couple energy graph illustrating cumulative care energy.

FIG. 12 is an Arndt-Schultz couple energy graph illustrating cumulative care energy. The Arndt-Schultz Law states that stimulation below a certain level is helpful for cell activation, but if excessive, such stimulation may cause cell depth.

As shown in FIG. 12, as the energy density (i.e., cumulative energy) increases, the activation level of the cell increases, but when the energy density exceeds a threshold (e.g., 4 J/cm$^2$ on the graph of FIG. 12), the activation level rapidly decreases and becomes worse than the steady state.

Since this threshold may vary depending on the user's situation, the present disclosure can control the light irradiator 260 to stop operation before the cumulative care energy reaches the threshold for stable operation of the hair dryer.

In a situation in which the amount of light emitted from the light irradiator 260 is designed to be 12 mW/cm$^2$, when the hair dryer is used for 4 minutes, the cumulative energy becomes 2.9 J/cm$^2$. In a situation in which a reference value is set to 29 J/cm$^2$ corresponding to about 70% of the experimental threshold, if the cumulative care energy exceeding the reference value is supplied to the hair dryer, the operation of the light irradiator 260 can be stopped (S140).

The current received from the iontophoresis electrodes 292 may enable resistance to be changed depending on the amount of moisture. If the amount of moisture is large, impedance between the iontophoresis electrodes 292 may decrease. As a result, the hair dryer can obtain a sufficient effect even when receiving only a low current as an input.

Therefore, when the amount of moisture is large, the level of current applied to the iontophoresis electrodes 292 is low. In the dried hair with the relatively low moisture content, the impedance is high, and the amount of current applied to the iontophoresis electrodes 292 is increased, thereby promoting the absorption of moisture and nutrients.

When the hair is almost dried and the moisture content is within the normal range (S122), the air volume can be set to "minimum" or "OFF", and the current amount of the iontophoresis module 270 can be set to a medium level (S132). If the cumulative care energy exceeds the reference value, the light irradiator 260 continuously senses the amount of moisture and adjusts the air volume and current amount of the iontophoresis module 270. When the cumulative care energy exceeds the reference value, the light irradiator 260 may terminate the care operation.

When the hair is completely dried (S121), the fan unit 170 can be turned off and the light irradiator 260 and the iontophoresis module 270 of the diffuser 200 can be controlled in a main care mode (S131).

Additionally, the expected drying time of the hair can be calculated based on the moisture content of the scalp. The drying speed may vary depending on the user's hair type or the amount of hair. Therefore, the expected time required for hair drying may be calculated based on the initial moisture content change, and the fan unit 170 and the temperature adjuster 160 can be controlled to adjust the air volume and temperature effective for hair drying.

As described above, the embodiments of the present disclosure can provide the hair dryer 100 that can effectively manage the user's scalp and hair.

The embodiments of the present disclosure can provide the hair dryer 100 that can effectively recognize the moisture status of the user's scalp and hair.

In addition, the embodiments of the present disclosure can provide the hair dryer 100 that can improve user convenience and efficiency by providing appropriate care means according to the condition of the user's scalp and hair.

Although a specific embodiment of the present disclosure has been illustrated and described above, those of ordinary skill in the art to which the present disclosure pertains will appreciate that various modifications are possible within the limits without departing from the technical spirit of the present disclosure provided by the following claims.

The invention claimed is:

1. A hair dryer comprising:

a main body including a gas outlet disposed at a front side of the main body so that gas is discharged outside through the gas outlet;

a handle extending from the main body; and a diffuser detachably coupled to the front side of the main body so that gas discharged from the gas outlet flows into the diffuser and is then discharged outside, wherein the diffuser includes:

a diffusing case, a rear side of which is coupled to the main body, configured to enable gas discharged from the gas outlet to flow into the diffusing case;

a circuit board including at least one pogo pin that is located at a front surface of the diffusing case and protrudes forward;

a discharge cover coupled to the front surface of the diffusing case and configured to include at least one gas discharge hole, a plurality of massage protrusions protruding forward, and a plurality of iontophoresis electrodes formed of a metal material; and an electrode connector disposed between the discharge cover and the circuit board and configured to electrically connect the pogo pin to the plurality of iontophoresis electrodes, and wherein the electrode connector includes:

a connection frame; and a connection electrode including a ring electrode located in a backward direction of the connection frame, and a branch electrode extending radially from the ring electrode.

2. The hair dryer according to claim 1, wherein:

the connection frame is formed in a ring shape that has an opening at a center thereof.

3. The hair dryer according to claim 2, further comprising:

a proximity sensor mounted on the circuit board and exposed through the opening of the connection frame.

4. The hair dryer according to claim 1, wherein the connection electrode includes:

a first connection electrode coupled to the connection frame; and a second connection electrode coupled to the connection frame so as not to contact the first connection electrode.

5. The hair dryer according to claim 4, wherein:

the ring electrode of the first connection electrode is located inside the ring electrode of the second connection electrode; and the branch electrode of the first connection electrode extends radially after being bent in a forward direction and is disposed at a position different from that of the branch electrode of the second connection electrode in forward and backward directions.

6. The hair dryer according to claim 5, wherein the plurality of iontophoresis electrodes includes:

a first iontophoresis electrode connected to the first connection electrode; and a second iontophoresis electrode connected to the second connection electrode, wherein a length of a protrusion from a back surface of the first iontophoresis electrode is shorter than a length of a protrusion from a back surface of the second iontophoresis electrode.

7. The hair dryer according to claim 4, wherein the pogo pin includes:

a first pogo pin connected to the ring electrode of the first connection electrode; and a second pogo pin connected to the ring electrode of the second connection electrode, wherein the first pogo pin and the second pogo pin are connected to power sources having different polarities.

8. The hair dryer according to claim 1, wherein:

the branch electrode is made of a metal material having elasticity.

9. The hair dryer according to claim 1, wherein the plurality of iontophoresis electrodes includes:

a first iontophoresis electrode connected to a power source having a positive (+) polarity;

a second iontophoresis electrode connected to a power source having a negative (−) polarity; and a controller configured to measure an amount of moisture in a scalp by measuring impedance between the first iontophoresis electrode and the second iontophoresis electrode.

10. The hair dryer according to claim 9, further comprising:

a temperature adjuster configured to control a temperature of the gas discharged through the gas outlet, wherein the controller controls the temperature adjuster so that the temperature of the gas discharged through the gas outlet increases as the amount of the moisture increases.

11. The hair dryer according to claim 9, further comprising:

a fan unit configured to control a speed of the gas discharged through the gas outlet, wherein the controller controls the fan unit so that the speed of the gas discharged through the gas outlet increases as the amount of the moisture increases.

12. The hair dryer according to claim 9, further comprising:

a light irradiator provided inside the diffusing case, and configured to emit light in a direction of the discharge cover, wherein the controller controls the light irradiator so that an amount of the light emitted by the light irradiator increases as the amount of the moisture increases.

13. The hair dryer according to claim 1, wherein:

a controller reduces an amount of current flowing through the plurality of iontophoresis electrodes as an amount of moisture increases.

14. The hair dryer according to claim 1, further comprising:

a light irradiator provided inside the diffusing case, and configured to emit light in a direction of the discharge cover; and a controller configured to deactivate the light irradiator when cumulative care energy generated depending on the amount of the light emitted from the light irradiator and a used time of the light irradiator exceeds a reference value.

* * * * *